(12) United States Patent  
Schwindt

(10) Patent No.: US 7,749,172 B2  
(45) Date of Patent: Jul. 6, 2010

(54) PNEUMATIC CIRCUIT

(75) Inventor: Jeffrey Schwindt, Indianapolis, IN (US)

(73) Assignee: Tissue Extraction Devices, LLC, Indianapolis, IN (US)

( * ) Notice: Subject to any disclaimer, the term of this patent is extended or adjusted under 35 U.S.C. 154(b) by 2031 days.

(21) Appl. No.: 10/461,315

(22) Filed: Jun. 13, 2003

(65) Prior Publication Data

US 2003/0199787 A1 Oct. 23, 2003

Related U.S. Application Data

(63) Continuation of application No. 10/420,197, filed on Apr. 22, 2003, now abandoned.

(60) Provisional application No. 60/374,952, filed on Apr. 23, 2002.

(51) Int. Cl.  
*A61B 10/00* (2006.01)  
*A61B 17/32* (2006.01)

(52) U.S. Cl. ............... 600/566; 600/567; 606/167

(58) Field of Classification Search ......... 600/564–568; 606/167, 170  
See application file for complete search history.

(56) References Cited

U.S. PATENT DOCUMENTS

| | | | |
|---|---|---|---|
| 3,659,605 A | 5/1972 | Sielaff | |
| 3,812,855 A | 5/1974 | Banko | |
| 4,274,411 A | 6/1981 | Dotson, Jr. | |
| 4,303,072 A | 12/1981 | Lewis | |
| 4,316,465 A * | 2/1982 | Dotson, Jr. | 604/22 |
| 4,560,323 A | 12/1985 | Orchard | |
| 4,604,089 A | 8/1986 | Santangelo et al. | |
| 4,662,869 A * | 5/1987 | Wright | 604/22 |
| 4,670,006 A | 6/1987 | Sinnett et al. | |
| 4,676,779 A | 6/1987 | Mayoral | |
| 4,795,428 A | 1/1989 | Hwang | |
| 4,850,423 A * | 7/1989 | Allen et al. | 165/5 |
| 5,125,901 A | 6/1992 | Lewis | |
| 5,176,628 A * | 1/1993 | Charles et al. | 604/22 |
| 5,176,629 A | 1/1993 | Kullas et al. | |
| 5,178,606 A | 1/1993 | Ognier et al. | |
| 5,380,280 A | 1/1995 | Peterson | |
| 5,520,652 A | 5/1996 | Peterson | |
| 5,676,650 A | 10/1997 | Grieshaber et al. | |
| 5,979,494 A * | 11/1999 | Perkins et al. | 137/487.5 |
| 6,039,724 A | 3/2000 | Seifert et al. | |
| 6,638,235 B2 * | 10/2003 | Miller et al. | 600/566 |

* cited by examiner

*Primary Examiner*—Max Hindenburg  
*Assistant Examiner*—Jonathan M Foreman

(57) ABSTRACT

A pneumatic circuit and other components are provided for the operation of a medical device. The pneumatic circuit provides controlled pressurized air to a medical device for use during a medical procedure.

13 Claims, 36 Drawing Sheets

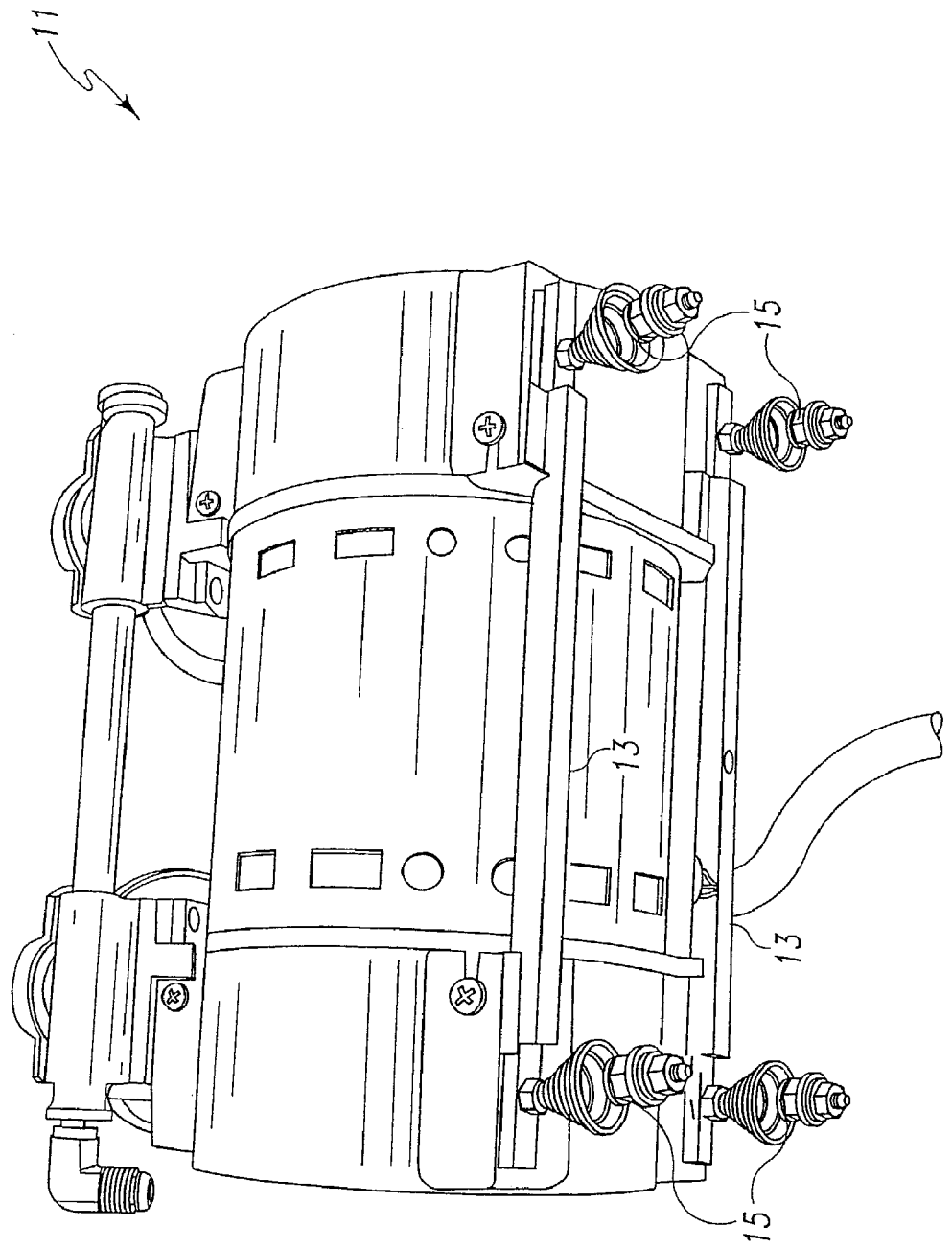

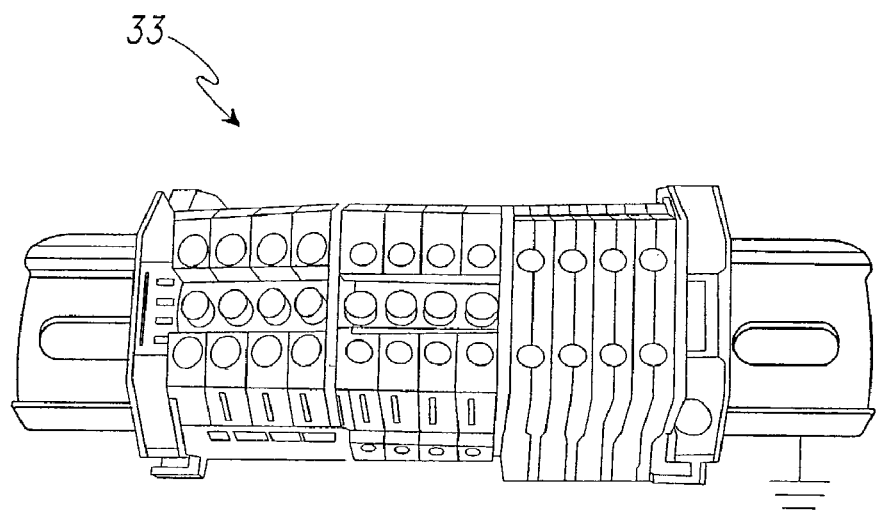
Fig. 14
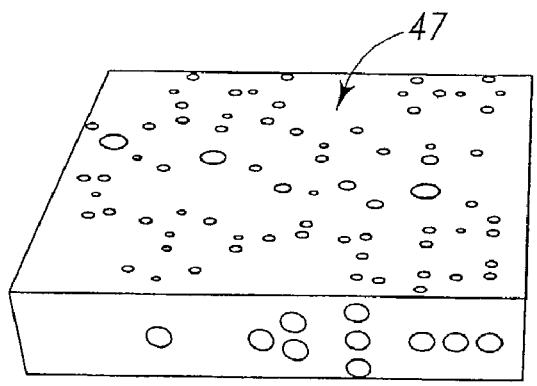 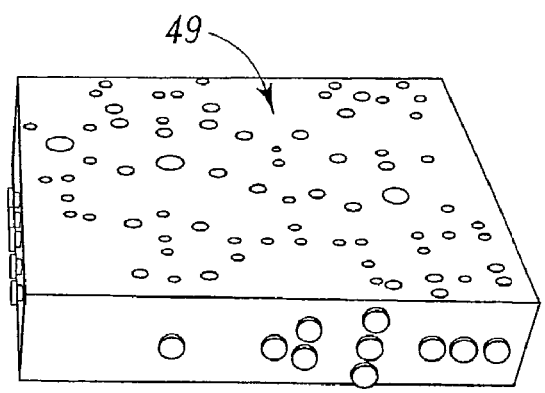
Fig. 15A  Fig. 15B

Fig. 34A

Kit List

ASE-1420-C CONTROL SYSTEM

| Part Name-# | Description | Quantity |
|---|---|---|
| fvs-361 | F-A FVS-361 SPECIAL 18SP-4 | 3 |
| fvs-362 | F-A FVS-362 SPECIAL 18DP-3 | 3 |
| nv-55 | FABCO NV-55 NEEDLE VALVE | 2 |
| 1020 | F-A 1020 COUPLER | 2 |
| mcd-1204 | CPC MCD-1204 COUPLER | 2 |
| zb2-bd2 | T-E ZB2-BD2 BLK SELECTR SWITC | 2 |
| zb2-bz009 | T-E ZB2-BZ009 MTG. RING | 2 |
| pxb-b1911 | T-E PXB-B1911 CONTACT BLOCK | 3 |
| pxb-b1921 | T-E PXB-1921 NP CONTACK BLK | 2 |
| pxv-m131 | T-E PXV-M131 GREEN INDICATOR | 1 |
| plm-a10 | T-E PLM-A10 MEMORY RELAY | 1 |
| pll-c10 | T-E PLL-C10 "AND" GATE | 1 |
| pln-c10 | T-E PLN-C10 NOT RELAY | 1 |
| plk-c10 | T-E PLK-C10 "OR" GATE | 6 |
| lfpul10/0.5 | T-E LFPUL10/0.5 PULSE VALVE | 1 |
| plk-a11 | T-E PLK-A11 "OR" ELEMENT | 1 |
| f-4200-60-mm | A-T F-4200-6-MM PRESSURE SWITCH | 1 |
| vp-701-30-mm | A-T VP-701-30-MM SWITCH | 1 |
| pp-701-30-mm | A-T PP-701-30-MM SWITCH | 1 |
| f-05-062 | A-T F-05-062 FILTER | 1 |
| k2-202e-n | RECTUS K2-202E-N COUPLER | 2 |
| k2-2027e-n | RECTUS K2-2072E-N COUPLER | 2 |
| n3-202e-m-n | RECTUS N3-202E-M-N PLUG | 2 |
| 20sfaw10mxns | RECTUS 20SFAW10MXNS | 2 |
| 88050-04 | ALPHA 88050-04 BULKHEAD CON. | 1 |
| 88800-53 | ALPHA 88800-53 CARTRIDGE | 38 |
| 88800-04 | ALPHA 88800-04 CARTRIDGE | 8 |
| 88000-53-02 | ALPHA 88000-53-02 STRT.ML.CON. | 1 |
| 88115-53-32 | ALPHA 88115-53-32 ML.SVL.ELBW. | 6 |
| 88110-04-02 | ALPHA 88110-04-02 ML.SVL.ELBW. | 2 |
| 88215-53-32 | ALPHA 8215-53-32 SWV BRCH TEE | 5 |
| 88700-04-53 | ALPHA 88700-04-53 REDUCER | 6 |
| 88310-53 | ALPHA 88310-53 UNION Y | 10 |
| 88310-04 | ALPHA 88310-04 UNION Y | 2 |
| 88230-53 | ALPHA 88230-53 UNION TEE | 3 |
| 88230-04 | ALPHA 88230-04 UNION TEE | 5 |
| 88040-04 | ALPHA 88040-04 UNION CON. | 2 |
| 88020-53-32 | ALPHA 88020-53-32 STRT.ML.CON. | 2 |
| al9840 | F-W AL9840 SPECIAL ASSEMBLY | 15 |
| bm-18 | ADSEN BM-18 MUFFLER | 7 |
| bm-08 | ADSEN BM-08 MUFFLER | 2 |
| .75-arsr-1.0 | L-A .75-ARSR-1.0 CYLINDER | 1 |

(Continued on following page)

Fig. 34B

Kit List

ASE-1420-C CONTROL SYSTEM

| Part Name-# | Description | Quantity |
|---|---|---|
| ro1-12a-k | M-I R01-12A-K REGULATOR | 2 |
| ro1-10a-k | M-I R01-10A-K REGULATOR | 1 |
| 11708 | M-I 11708 ADAPTER | 3 |
| 204-2209-2 | M-I 204-2209-2 FILTER | 1 |
| 104-3101-2 | M-I 104-3101-2 RELIEF REG. | 1 |
| cds-4p-004d | D-F CDS-4P-004D GAUGE | 2 |
| cds-4p-010d | D-F CDS-4P-010D GAUGE | 2 |
| 122a-2x2 | ALKON 122A-2X2 1/8" HEX NIPPLE | 3 |
| 100a-2 | ALKON 100A-2 1/8" UNION ELBOW | 3 |
| plj-1/4" | PISCO PLJ-1/4" ELBOW | 3 |
| mcv-1 | CLIPPARD MCV-1 VALVE | 2 |
| 5a708 | GRAINGER 5A708 RELIEF VALVE | 1 |
| al445 | GAST AL445 MUFFLER | 1 |
| 0353-6-6 | PARKER 0353-6-6 BULKHEAD | 1 |
| 0253-4-6 | PARKER 0253-4-6 BULKHEAD | 1 |
| 2303-6-6 | PARKER 2303-6-6 ELBOW | 1 |
| 2103-4-6 | PARKER 2103-4-6 ELBOW | 2 |
| 2203-4-6 | PARKER 2203-4-6 ELBOW | 1 |
| 919-0639-6-6-6 | PARKER 919-0639-6-6-6-10" | 1 |
| 919-0606-6-6-6 | PARKER 919-0606-6-6-6-14" | 1 |
| 919-0606-6-6-6- | PARKER 919-0606-6-6-6-19" | 1 |
| 3p-30a2-s | L-M 3P-30A2-S FOOT SWITCH | 1 |
| g.75x2whg | PANDUIT G. 75X2WHG DUCT | 5 |
| c.75whg | PANDUIT C. 75WHG COVER | 5 |
| cc072x38x1s | L-S CC072X38X1S SPRING | 8 |
| 5692t24 | M-C 5692T24 FOAM | 4 |
| 91843a118 | M-C 91843A118 ROUND NUT | 1 |
| 93505a850-6/32 | M-C 93505A850-6/32 STAND OFF | 2 |
| 6120g1an | LYTRON 6120G1AN HEAT EXCHANGER | 1 |
| 11845a11 | M-C 11845A11 HOOK | 1 |
| 81f8103 | NEWARK 81F8103 FAN | 5 |
| 81f2738 | N-W 81F2738 GUARD | 5 |
| 81f2747 | N-W 81F2747 POWER CORD | 5 |
| 64f276 | N-W 64F276 SIGNAL | 1 |
| 16f9371 | N-E 16F9371 10 AMP FILTER | 1 |
| a2207-11 | AIC A2207-11 ENTRY MODULE | 1 |
| 800em-lfa3 | A-B 800EM-LFA3 OPERATOR | 1 |
| 800e-2dl5g | A-B 800E-2DL5G MODULE | 1 |
| 800e-2x10 | A-B 800E-2X10 CONTACT | 2 |
| 3p | H-P 3P AIR VALVE | 1 |
| 3822-03-5287 | SPARTAN 3822-03-5287 VALVE | 2 |
| ase-1420-c | ASE-1420-C CONTROL SYSTEM | 1 |

Fig. 34C

ASE-1420 PARTS SUPPLIERS

| MANUFACTURER | ABBREVIATION | CITY, STATE | PARTS PROVIDED |
|---|---|---|---|
| FABCO-AIR | F-A | GAINESVILLE, FL | 3&4 WAY VALVES, NEEDLE VALVES |
| COLDER PRODUCTS | CPC | ST. PAUL, MN | HANDPIECE QUICK DISCONNECTS |
| TELEPNEUMATIC/PARKER | T-E | RICHLAND, MI | LOGIC COMPONENTS & FOOT SWITCH |
| AIRTROL | A-T | NEW BERLING, WI | PRESSURE & VACUUM SWITCHES |
| RECTUS/TEMA | RECTUS | SPARTA, NJ | FT SWITCH QUICK DISCONNECTS |
| ALPHA TECHNOLOGIES | ALPHA | FRANKLIN, TN | FITTINGS |
| FREELIN-WADE | F-W | MCMINNVILLE, OR | TUBING |
| ADSENS | ADSEN | CITY OF INDUSTRY, CA | MUFFLERS |
| LIN-ACT/PARKER | L-A | DES PLAINES, IL | VOLUME CHAMBER |
| MONNIER | M-I | ALGONAC, MI | REGULATORS AND FILTERS |
| DYNAMIC FLUID COMPONENTS | D-F | WEST UNION, SC | GAUGES |
| ALKON CORPORATION | ALKON | CHICAGO, IL | BRASS FITTINGS |
| CLIPPARD | CLIPPARD | CINCINNATI, OH | CHECK VALVES |
| GRAINGER | GRAINGER | INDIANAPOLIS, IN | RELIEF VALVE |
| GAST MFG | GAST | BENTON HARBOR, MI | PUMPS |
| PARKER FITTINGS | PARKER | WICKLIFFE, OH | HIGH TEMP HOSES |
| PANDUIT | PANDUIT | TINLEY PARK, OH | WIRE DUCT |
| LEE SPRING | L-S | BROOKLYN, NY | MOTOR MOUNTS |
| MCMASTER-CARR | M-C | CHICAGO, IL | ACOUSTICAL FOAM |
| LYTRON | LYTRON | BOSTON, MA | HEAT EXCHANGER |
| NEWARK ELECTRONICS | N-W | PALATINE, IL | FANS, BREAKER, POWER ENTRY, FILTER |
| ALLEN-BRADLEY/ROCKWELL | A-B | MILWAUKEE, WI | TERMINALS, ON/OFF SWITCH |
| SPARTAN SCIENTIFIC | SPARTAN | BOARDMAN, OH | DUMP VALVES |
| HUMPHREY PRODUCTS | H-P | KALAMAZOO, MI | TEST BUTTON VALVE |
| STANDARD CHANGE MAKERS | SCM | INDIANAPOLIS, IN | CABINET |
| JWS MACHINE | JWS | BRAZIL, IN | MANIFOLDS AND OTHER MACHINED PARTS |

//

PNEUMATIC CIRCUIT

This application is a continuation application of U.S. Ser. No. 10,420,197 filed Apr. 22, 2003 now abandoned, which claims priority to provisional patent application No. 60/374,952 filed Apr. 23, 2002. The disclosures of all of these prior applications are expressly incorporated by reference herein.

BACKGROUND OF THE INVENTION

The present invention relates to a pneumatic circuit, and particularly to a pneumatic circuit for use in the operation of an at least partially air-powered tool. More particularly, the present invention relates to a pneumatic circuit useful in the pneumatic operation of a medical device.

SUMMARY OF THE INVENTION

The present invention relates to one or more of the following features, elements or combinations thereof. A pneumatic control system is provided for use with a medical device, illustratively a suction biopsy device. The suction biopsy device has a cannula for insertion into a body to a point adjacent to a mass to be examined, and a rotating cutter device is housed within. The cannula has an orifice, and a pneumatic cylinder is coupled to the cutter for moving the cutter relative to the orifice.

A rinse or illustratively saline solution is provided for assisting in the removal of the mass to be examined. A suction is provided for assisting in the removal of the mass to be examined. The control system has an absence of electrical circuitry configured to control the operation of the suction biopsy device. Electrical power is illustratively provided only for the compressor and the vacuum.

The cannula defines an axis and the cutter is illustratively aligned coaxially with the cannula for rotation about the axis. A pneumatic motor actuates the rotational movement of the cutter. The pneumatic cylinder causes the cutter to move axially relative to the cannula.

A method of removing a tissue mass from a body is also provided. The method comprises the steps of inserting a hollow cannula having an aperture into the body such that the aperture is positioned adjacent to the tissue mass. Suction is provided to the cannula such that a portion of the tissue mass is pulled inside the cannula through the aperture. The cutter is pneumatically caused to move relative to the aperture so that the cutter cuts the portion of tissue mass from the remainder of the tissue mass. The cut portion of tissue mass is then transported through the cannula with the provided suction. The pneumatic movement of the cutter is controlled by a pneumatic circuit comprising a pressure sensor.

The control system drives a cutter blade connected to the biopsy device. The cutter blade moves from a recessed position to an extended position. The control system cycles the cutter between the recessed position and the extended position at a predetermined cycle rate, responding to user commands when determining whether to continue to cycle.

A pneumatically driven motor rotates the cutter. A pneumatically driven piston moves the cutter between the recessed position and the extended position. Pressurized gas is delivered to the pneumatic motor, and a saline supply is delivered to the cannula.

Suction assists in removing the mass from the body during a surgical procedure. The control system is configured to run continually but have cyclical elements responding to the continual operation.

Additional features of the disclosure will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which:

FIG. 4 is a view of an air compressor shown upside down with tie-down rails and springs attached;

FIG. 14 is a view of the terminal block subassembly;

FIGS. 15A-B are perspective views of the two manifolds configured to route the pneumatic tubing within the console;

FIGS. 34A-C show parts listings of the various parts used in the construction of the Breast Biopsy System.

DETAILED DESCRIPTION OF THE DRAWINGS

Figure 1:
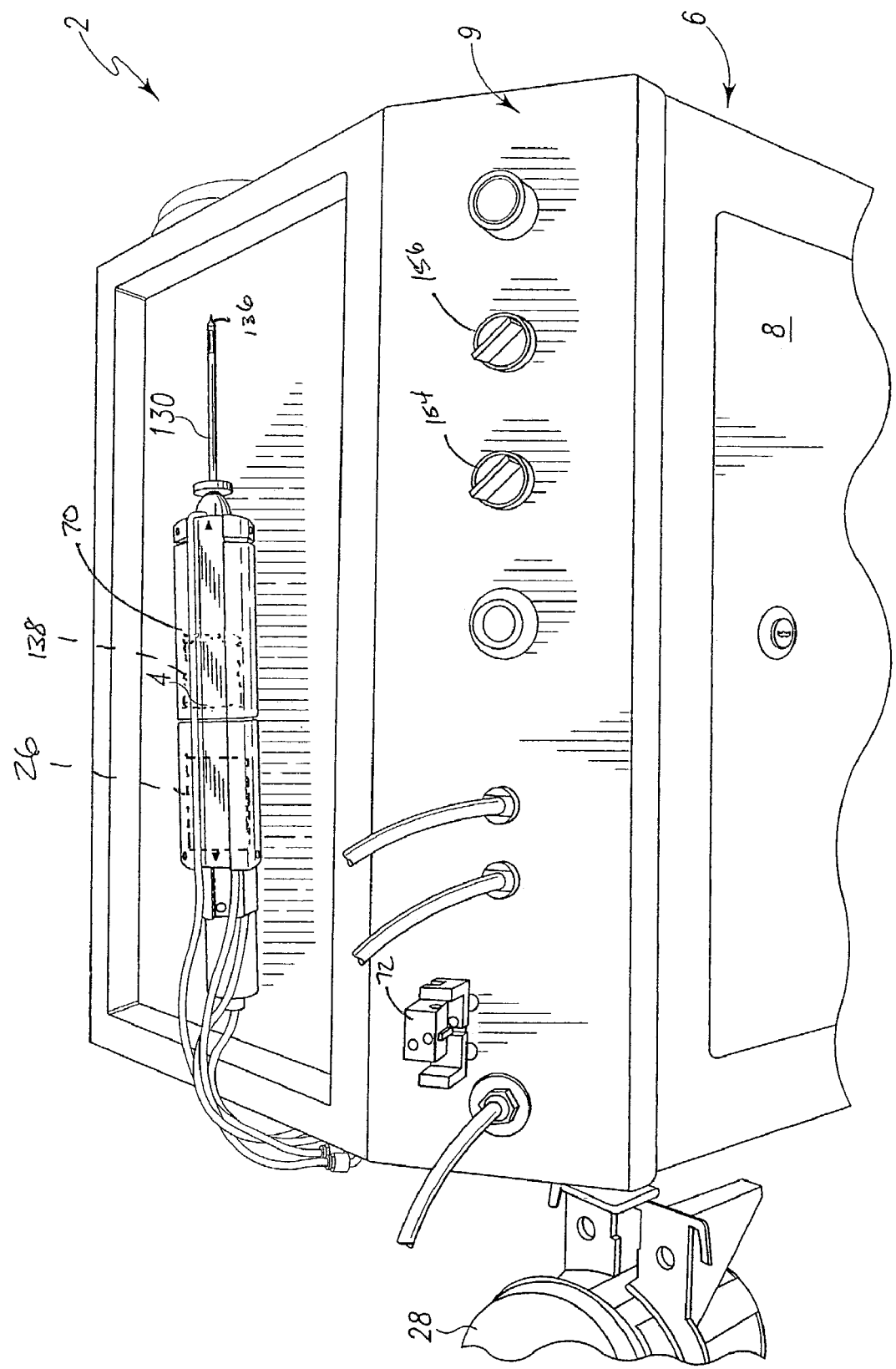
FIG. 1 is a top perspective partial view of a Breast Biopsy System having a hand wand, the Biopsy System including a pneumatic circuit internally, the circuit configured to operate the Biopsy System and hand wand.
Figure 2:
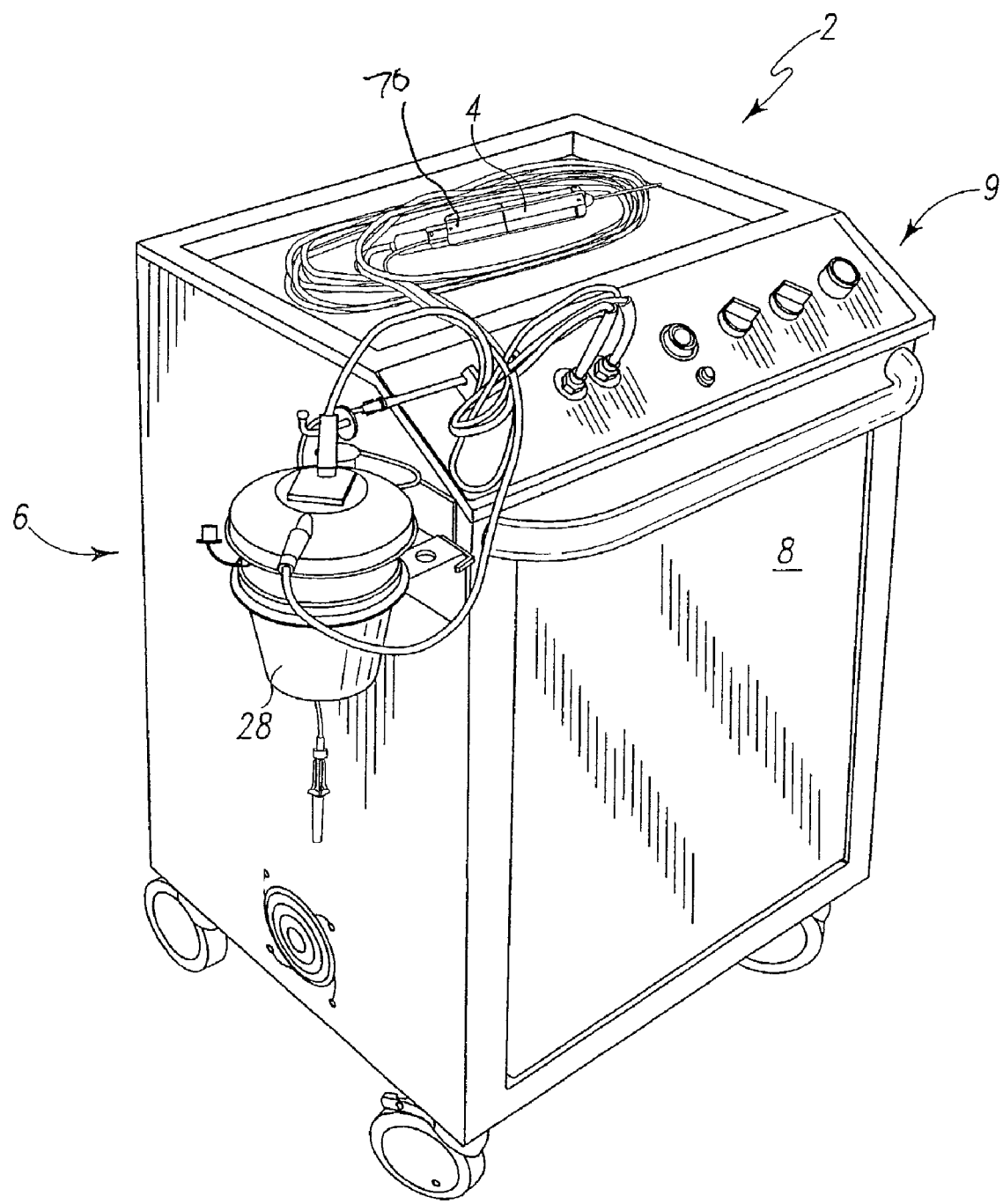
FIG. 2 is a perspective view of the system shown in FIG. 1.
Figure 17:
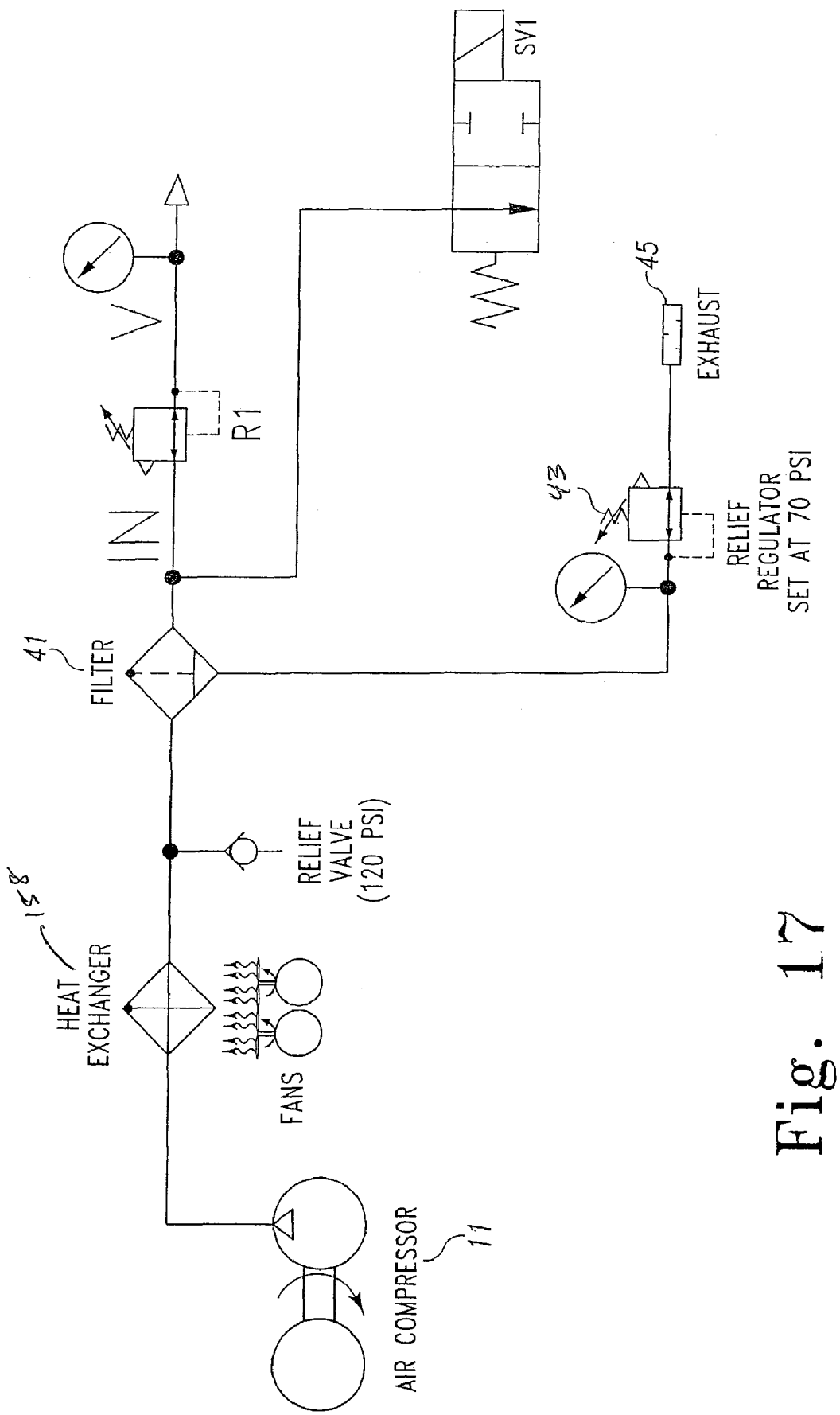
FIG. 17 is a schematic representation of an evaporation valve portion of the pneumatic circuit.
Figure 18:
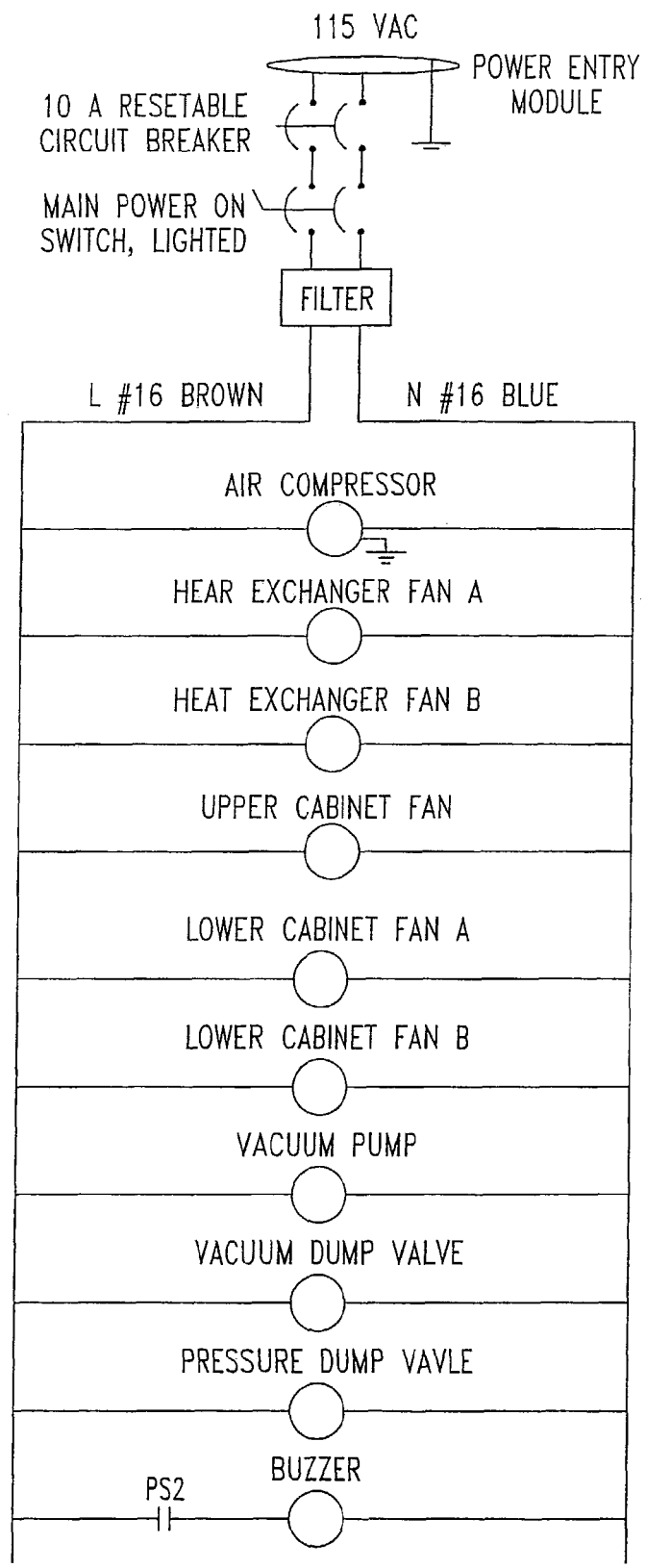
FIG. 18 is another schematic representation of a portion of the pneumatic circuit.
Figure 19D:
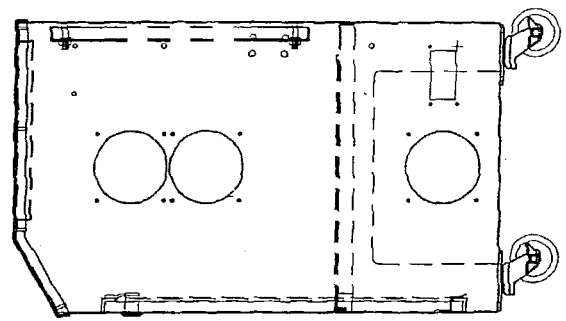
FIGS. 19A-D show specification drawings for the console.
Figure 19B:
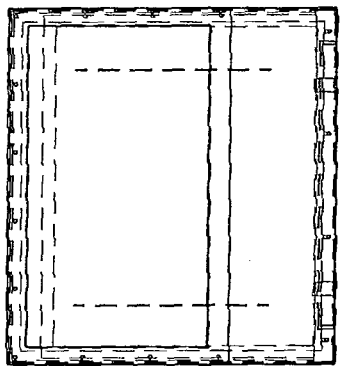
Figure 19C:
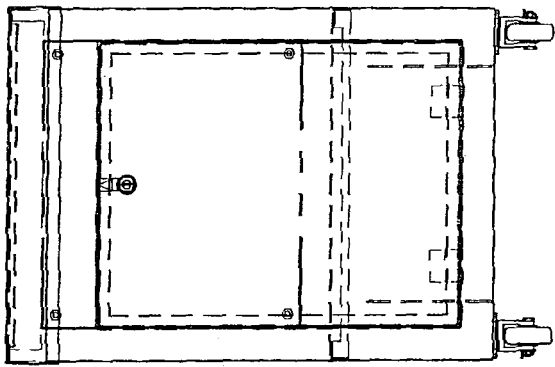
Figure 19A:
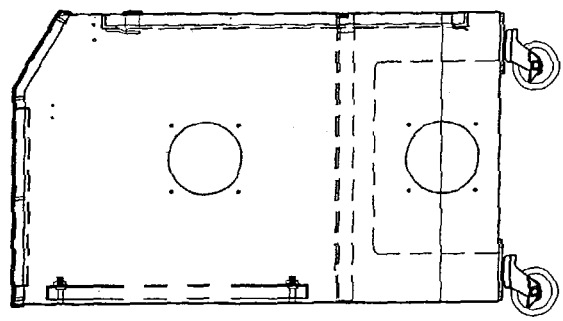
Figure 20A:
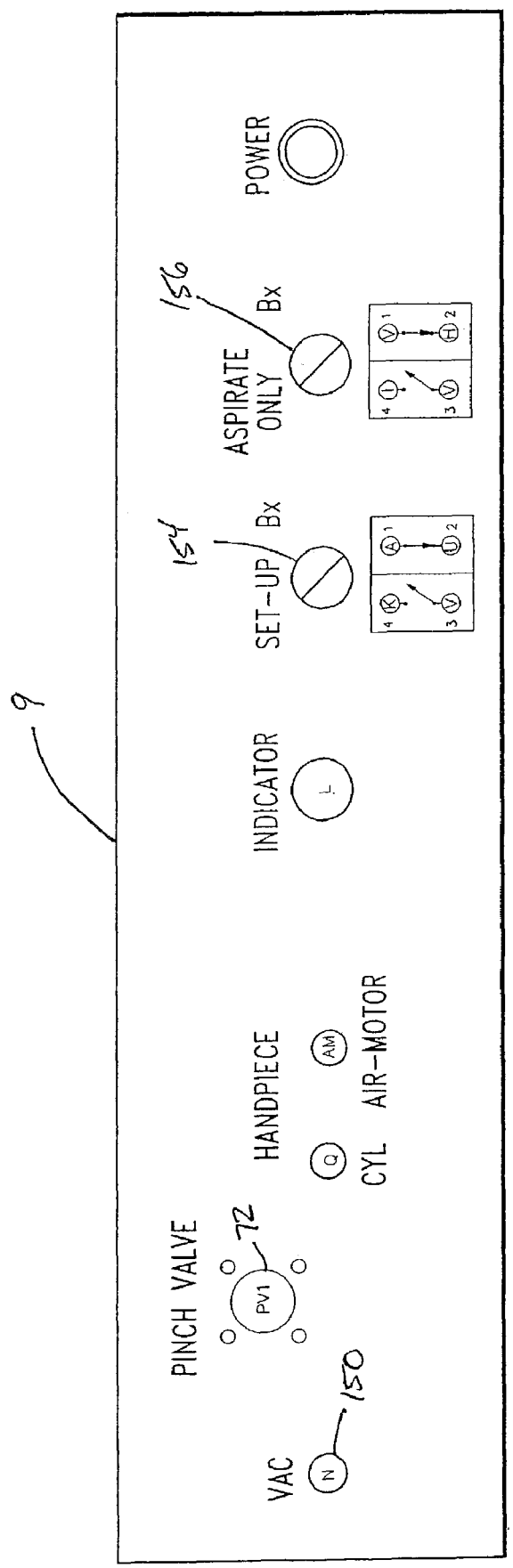
FIG. 20A shows the configuration of the control panel.
Figure 20B:
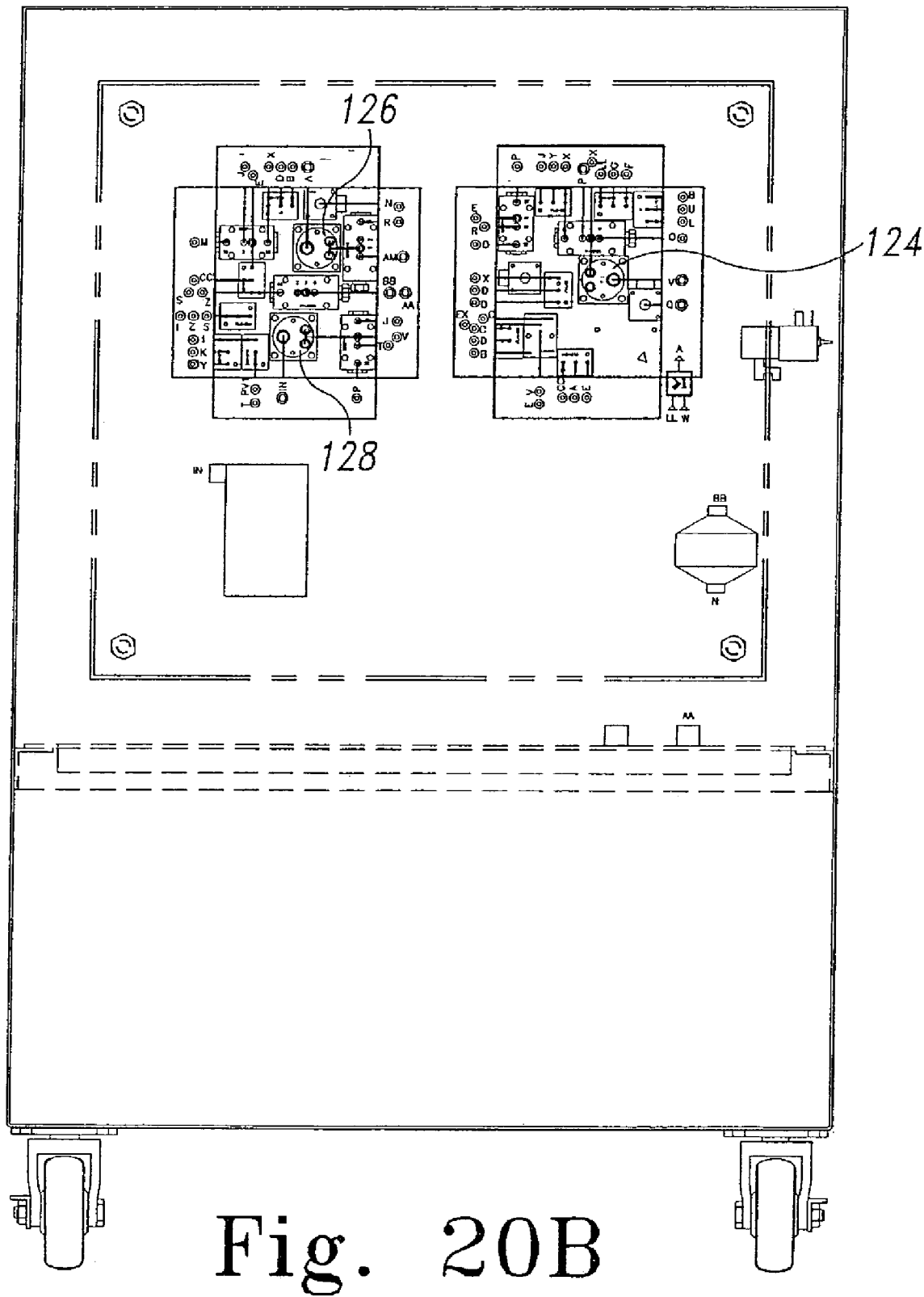
FIG. 20B shows the configuration of the manifolds with relation to the filters and connection points.
Figure 21A:
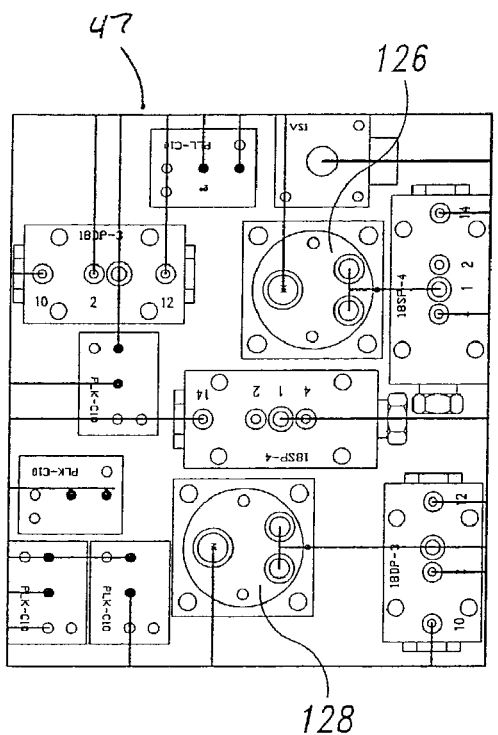
FIGS. 21A-D show diagrammatic representations of the manifolds depicting the ports and internal passageways associated with the manifolds.
Figure 21B:
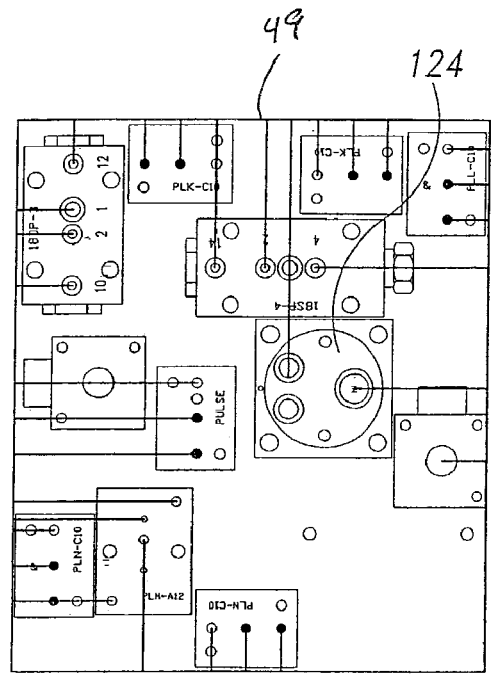
Figure 21C:
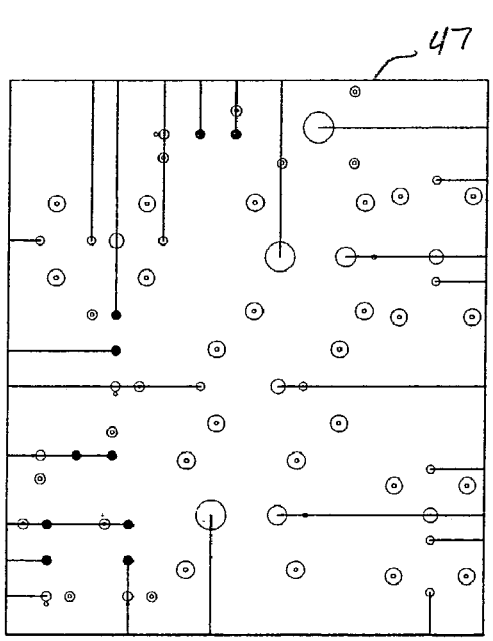
Figure 21D:
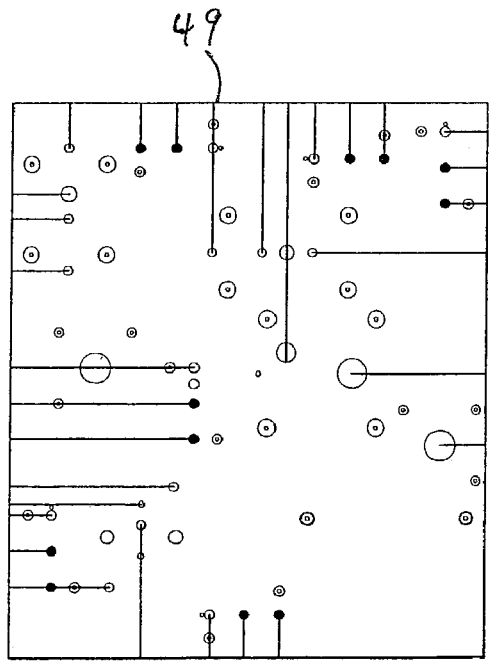

One embodiment of the present disclosure is shown in FIGS. 1 and 2 in the form of a Breast Biopsy System 2 having a hand wand 4. Biopsy System 2 illustratively includes a console 6 having an access door 8 and a control panel 9 positioned toward the top of the console 6. Biopsy System 2 includes an internal pneumatic circuit 10 (shown in FIGS. 8-12 and schematically in FIGS. 16-18) that is configured to operate a medical device 70, illustratively hand wand 4, as will be discussed in more detail below. It should be understood that as used herein, medical device 70 can be any medical device that is powered at least in part by pneumatic pressure. The illustrative medical device 70 comprises a hand wand 4, and such terms are used interchangeably throughout.

Figure 3A:
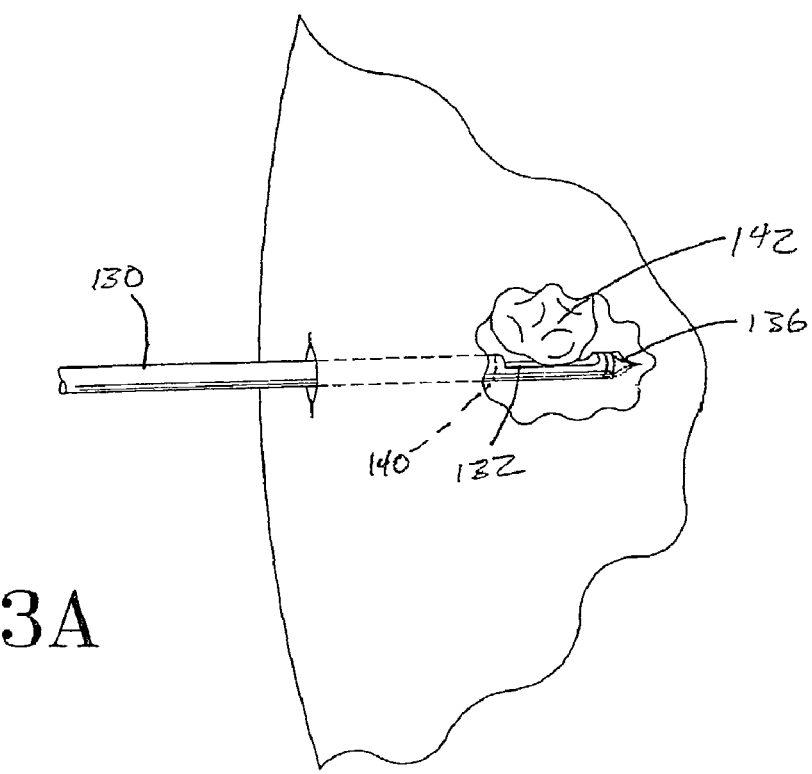
FIG. 3A is a view of the cannula of the hand wand inserted into a patient's breast adjacent a tissue mass, the cannula having an aperture positioned adjacent the mass.
Figure 3B:
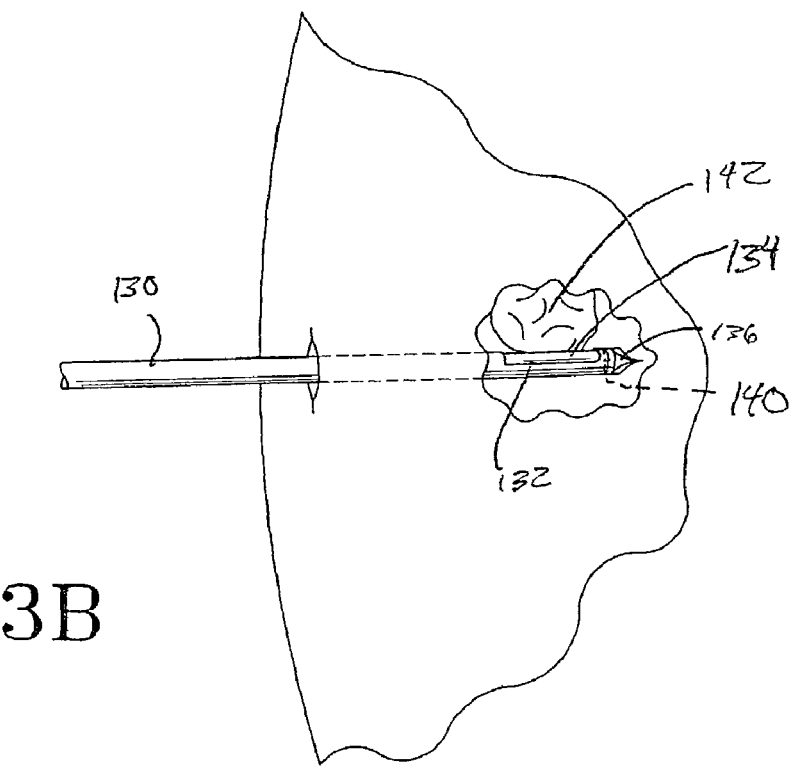
FIG. 3B is a view similar to that of FIG. 3A, showing a cylindrical cutter that has moved inside the cannula, thereby cutting away a portion of the tissue mass.

Biopsy System 2, and particularly hand wand 4, illustratively function in the following manner. A patient having a mass 142 to be removed receives a local anesthetic and the mass is identified and located in the patient. Location methods may include ultrasound, magnetic resonance imaging (MRI), X-Ray, or any other method known in the medical industry. As can be seen in FIGS. 1 and 3A-B, hand wand 4 illustratively includes a hollowed needle or cannula 130 extending therefrom, the cannula 130 having a sharp distal end 136 for facilitating piercing into the patient's body, and the cannula 130 further having a cutter 134 positioned therein for rotational and axial movement relative to the cannula 130. Cutter 134 is illustratively a cylindrical blade, but other configurations are within the scope of the disclosure. Distal end 136 is illustratively a frusto-conical stainless steel tip pressfitted on the end of cannula 130, the tip having a plastic cutting board (not shown) housed within for receiving cutter 134 when cutter 134 is at its full stroke position.

An aperture 132 is illustratively formed in the cylindrical wall of cannula 130 at its distal end. During operation, as shown in FIGS. 3A-B, a physician inserts cannula 130 into the patient (i.e. the cannula is inserted into a woman's breast) such that aperture 132 is positioned proximal to a mass 142 to be removed. While the cannula is being inserted into the patient's body, the cylindrical cutter 134 is positioned inside cannula 130 such that cutter 134 substantially closes off aperture 132. Pneumatic circuit 10 directs compressed air to pneumatic cylinder 26 in order to position cutter 134 at its full stroke position.

After cannula 130 is in position in the patient's body, pneumatic circuit 10 directs the retracting and advancing movement of cutter 134 relative to the cannula 130 in response to signals from a foot switch 16, a remote push button 18, or a panel push button 18A (see FIG. 16B) operated by a medical technician or surgeon. Once the operator signals for the cutting to begin, pneumatic circuit 10 directs vacuum pressure to hand wand 4, and pneumatic circuit releases the compressed air from pneumatic cylinder 26 (which is illustratively housed in hand wand 4). Once compressed air is released from pneumatic cylinder 26, a spring urges the plunger in pneumatic cylinder 26 toward the retracted position, thereby causing cutter 134 to move to the retracted position, consequently opening aperture 132. Vacuum pressure is also applied by pneumatic circuit 10 to the inside of cannula 130, causing a portion of the mass 142 to be drawn inside cannula 130. While the portion of the mass 142 is drawn inside cannula 130, pneumatic circuit 10 sends compressed air to cylinder 26, thereby moving cutter 134 relative to aperture 132 toward the extended, full-stroke position. At substantially the same time, pneumatic circuit 10 further directs compressed air toward a pneumatic motor 138 housed in hand wand 4. Pneumatic motor 138 is coupled to cutter 134 and causes cutter 134 to rotate about its axis inside cannula 130. As a result of the rotational and axial movement of cannula 130, cutter 134 cuts the portion of the mass 142 that extends inside the cannula 130 as cutter moves toward distal end 136 of cannula 130.

Once cutter 134 has completed such a cycle and has returned to the position wherein aperture 132 is closed, pneumatic circuit 10 confirms whether further cutting will be necessary. Such confirmation is received from foot switch 16 or remote push button 18/panel push button 18A, described further herein. In the illustrated embodiment, a short pause of approximately a half second prior to confirmation allows sufficient time for an operator to determine whether additional cutting will be necessary.

If additional cutting is not deemed to be required and the mass 142 is considered removed, the operator removes cannula 130 from the patient's body. If instead confirmation is made that additional cutting is required, pneumatic cylinder 26 causes cutter 134 to again move to the retracted position, thereby opening the aperture 132, and saline is directed through the hand wand 4 and between cannula 130 and cutter 134. Saline passing over the cutting end 140 of cutter 134 is suctioned into the central portion of the cannula 130 with urging from the aforementioned applied vacuum pressure. Suctioning saline through the central portion of cannula 130 serves to flush the cut portion of the mass through the cannula toward a waste canister 28, described further herein. Additionally, the saline serves as a lubricant between the cannula 130 and the cutter 134. In the illustrative embodiment, pneumatic motor 138 is not actuated while cutter 134 is moved toward the retracted position, therefore cutter 134 does not rotate relative to cannula 130 during this retraction phase. Such operation is desirable so that tissue does not wrap around cutter 134 as cutter 134 retracts.

Pneumatic circuit 10 directs the continuous above-described cycling of cutter 134 as long as foot switch 16 or remote push button 18 or panel push button 18A is depressed. Illustratively, ultrasound, magnetic resonance imaging (MRI), or other mass-locating methods known in the art may be used during the procedure in order to monitor the progress of the removal of the mass 142. It is advantageous that Breast Biopsy System 2, in one embodiment, can be used in conjunction with an MRI device because of the majority of its components being pneumatic and non-magnetic.

Figure 5:
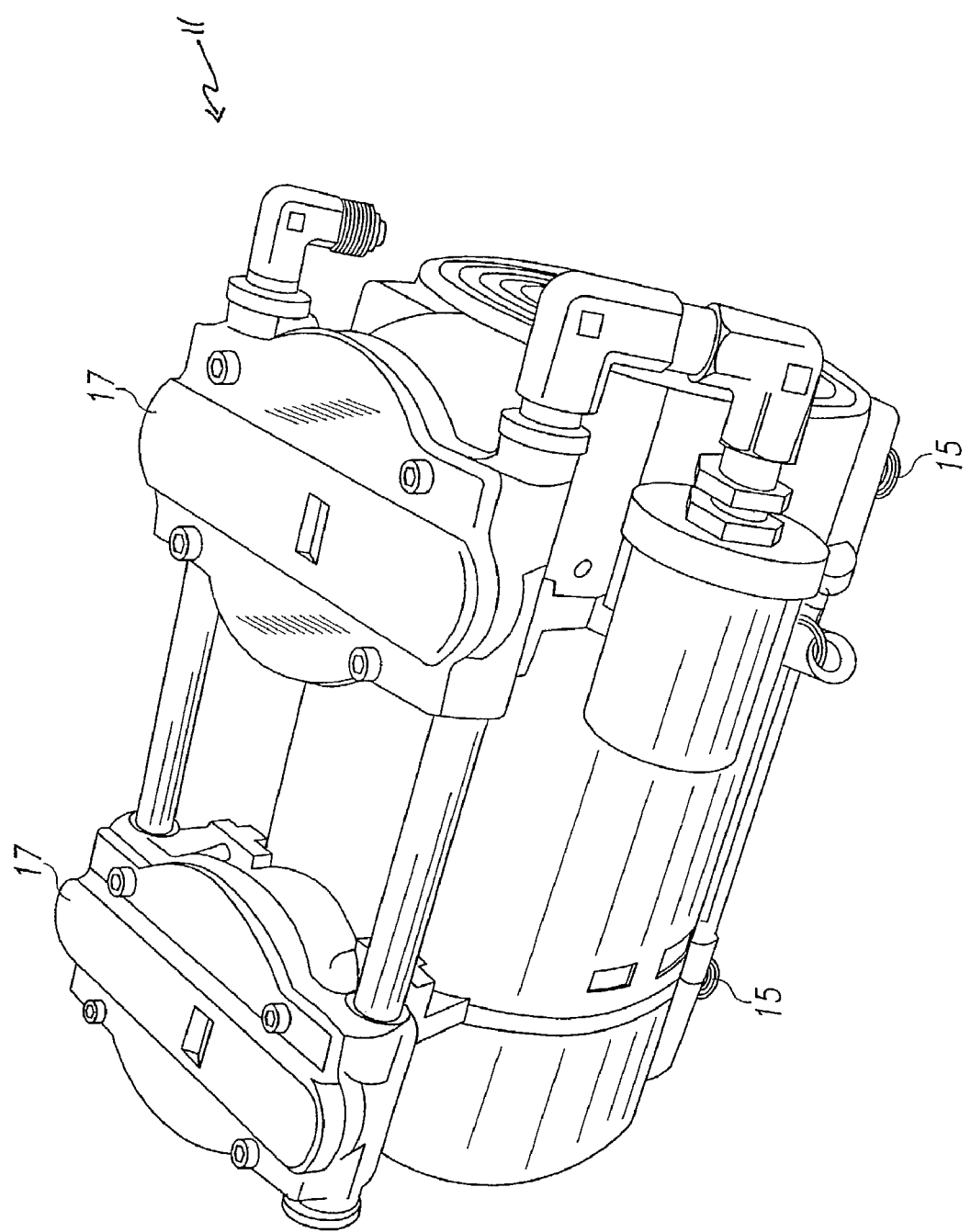
FIG. 5 is a view of the compressor of FIG. 4, showing the compressor right side up with additional fittings.
Figure 7:
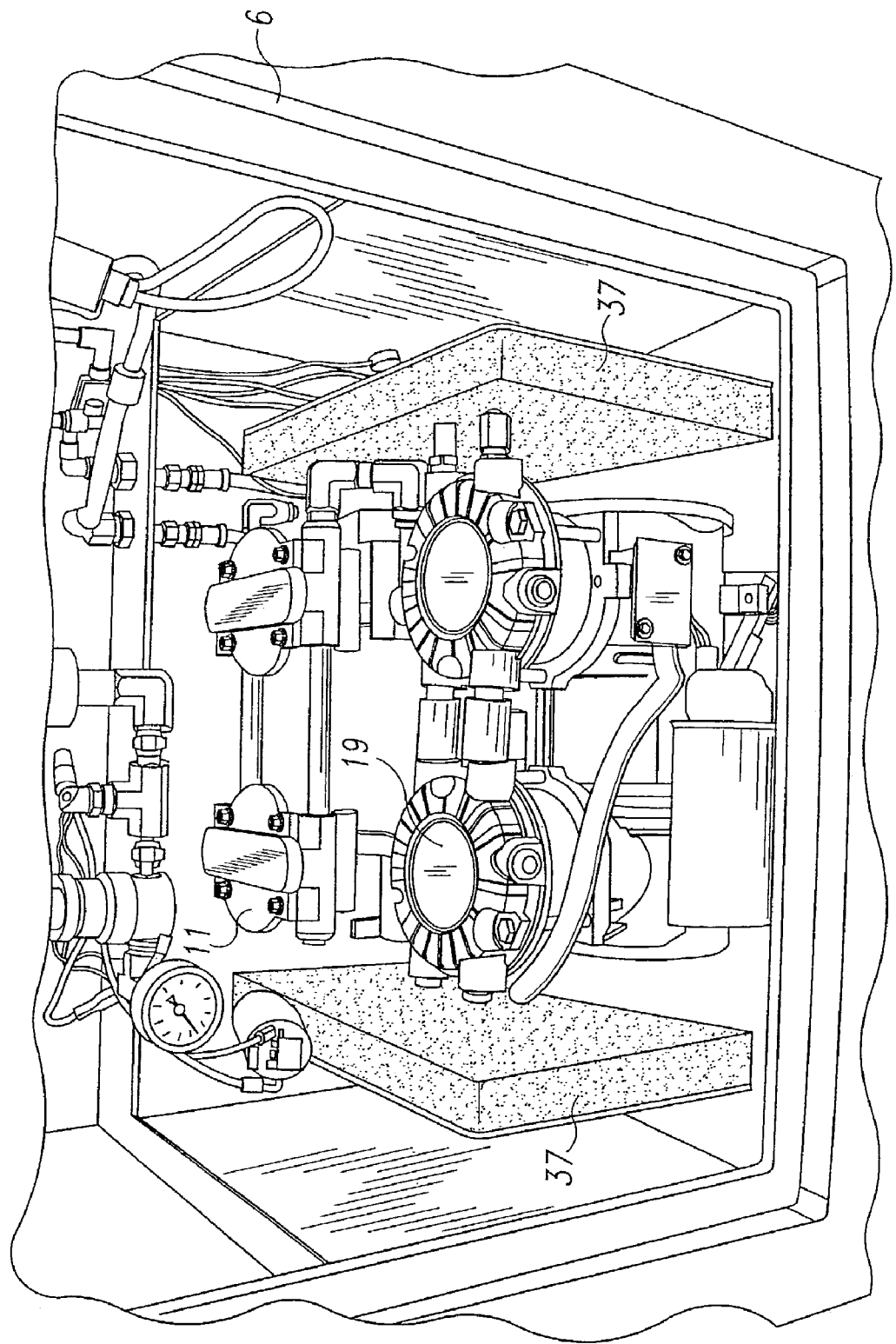
FIG. 7 is a view of the compressor of FIGS. 4-5 and the vacuum pump of FIG. 6 both installed in a console.

The components comprising pneumatic circuit 10, and their associated functions in the control of hand wand 4, are described below. FIGS. 4 and 5 show views of an air compressor 11 having tie-down rails 13 and springs 15 attached thereto. Fittings 17 are coupled to the top of air compressor 11 as shown in FIG. 5, and air compressor 11 is illustratively mounted in the rear of the console 6 as shown in FIG. 7.

Figure 6:
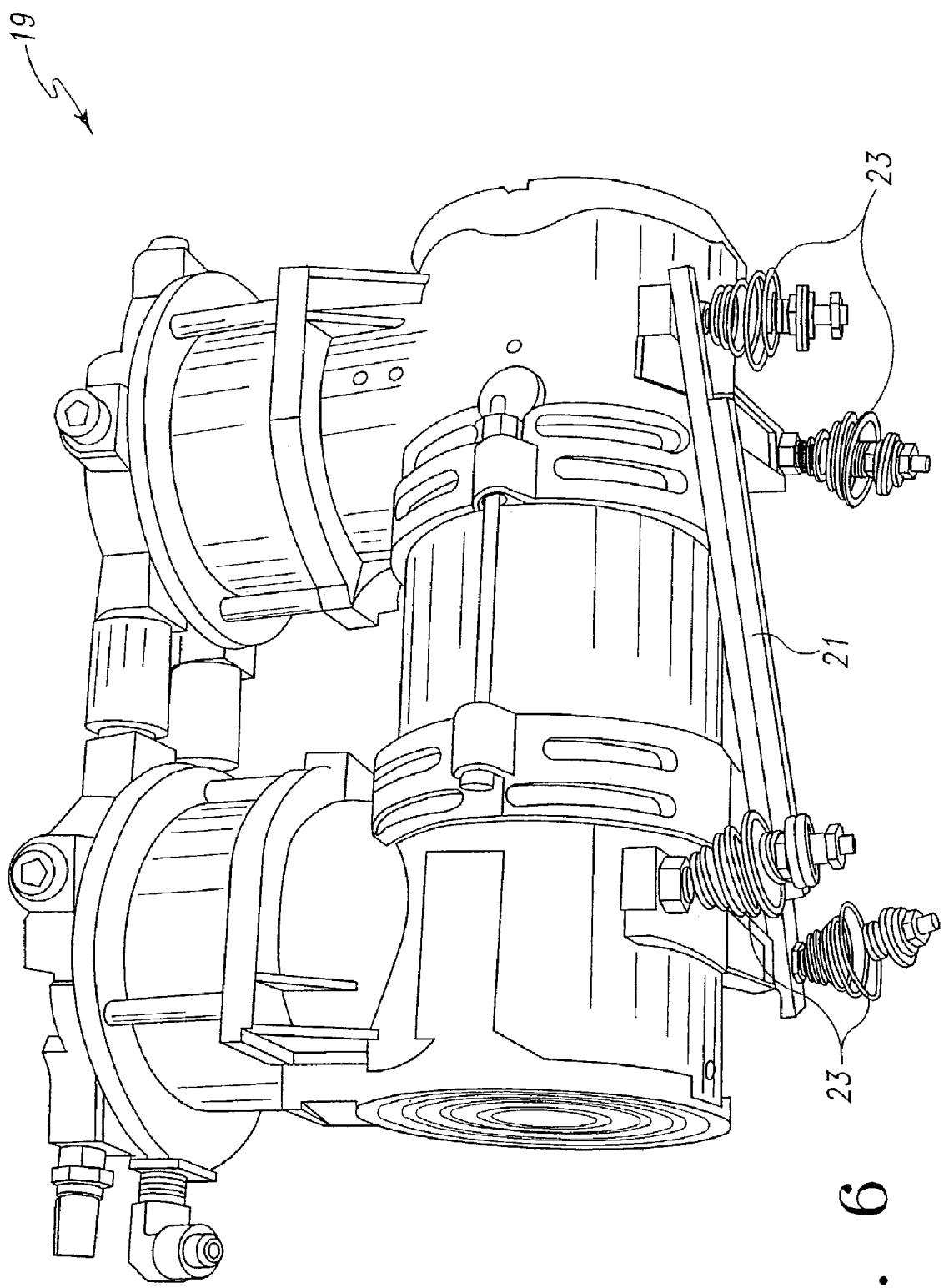
FIG. 6 is a view of a vacuum pump showing the tie-down rail and springs.

A vacuum pump 19 is shown in FIG. 6, the vacuum pump having a tie-down rail 21 and springs 23. FIG. 7 shows the relative placement of vacuum pump 19 and air compressor 11 in the lower portion of console 6. Soundproofing material 37 is also placed in the proximity of vacuum pump 19 and air compressor 11 in order to muffle the sound of air compressor 11 and vacuum pump 19 during operation.

Figure 8:
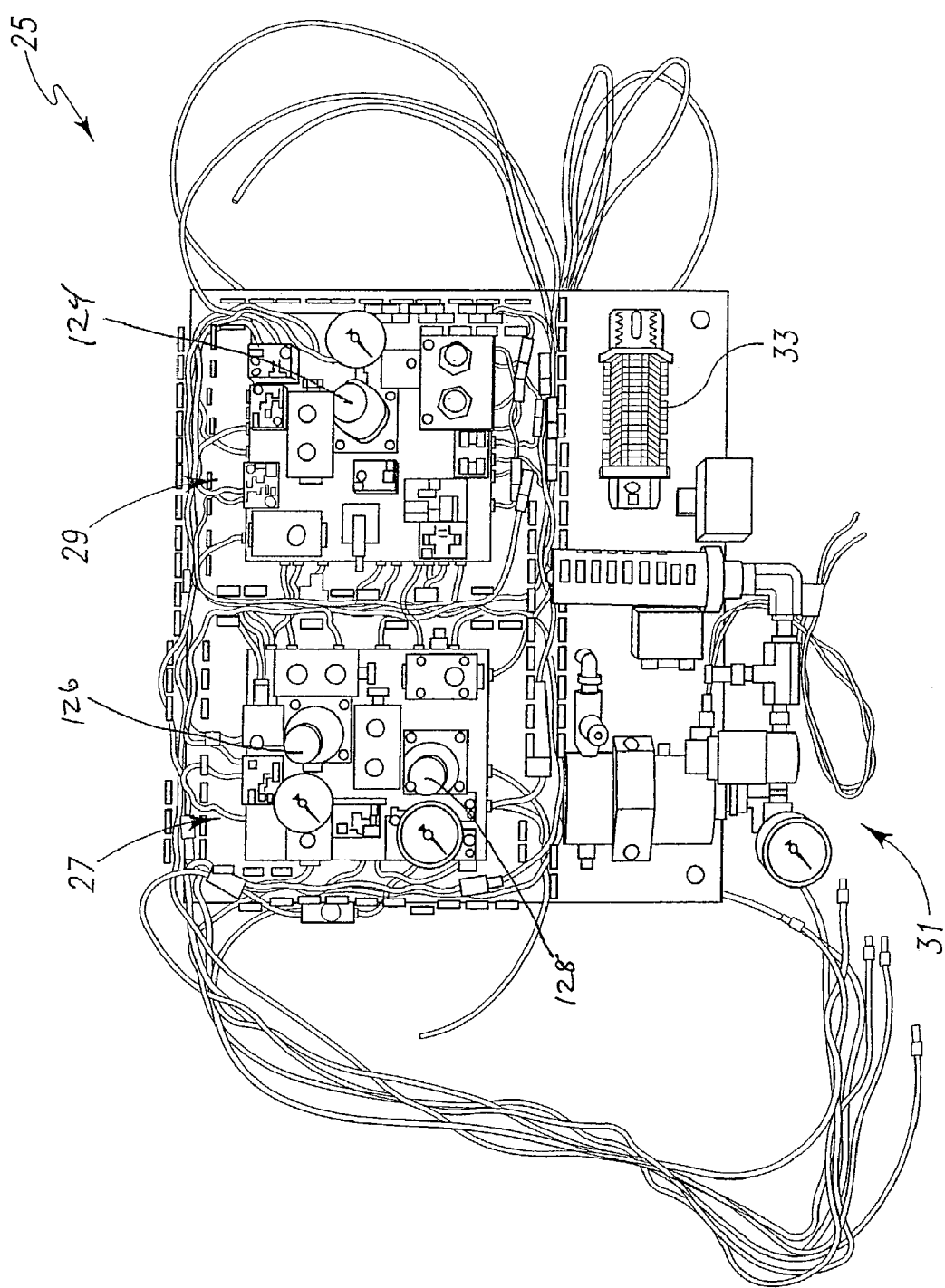
FIG. 8 is a view of a console mounting panel showing manifold subassemblies, a filter subassembly, and a terminal block subassembly mounted on the mounting panel.
Figure 9:
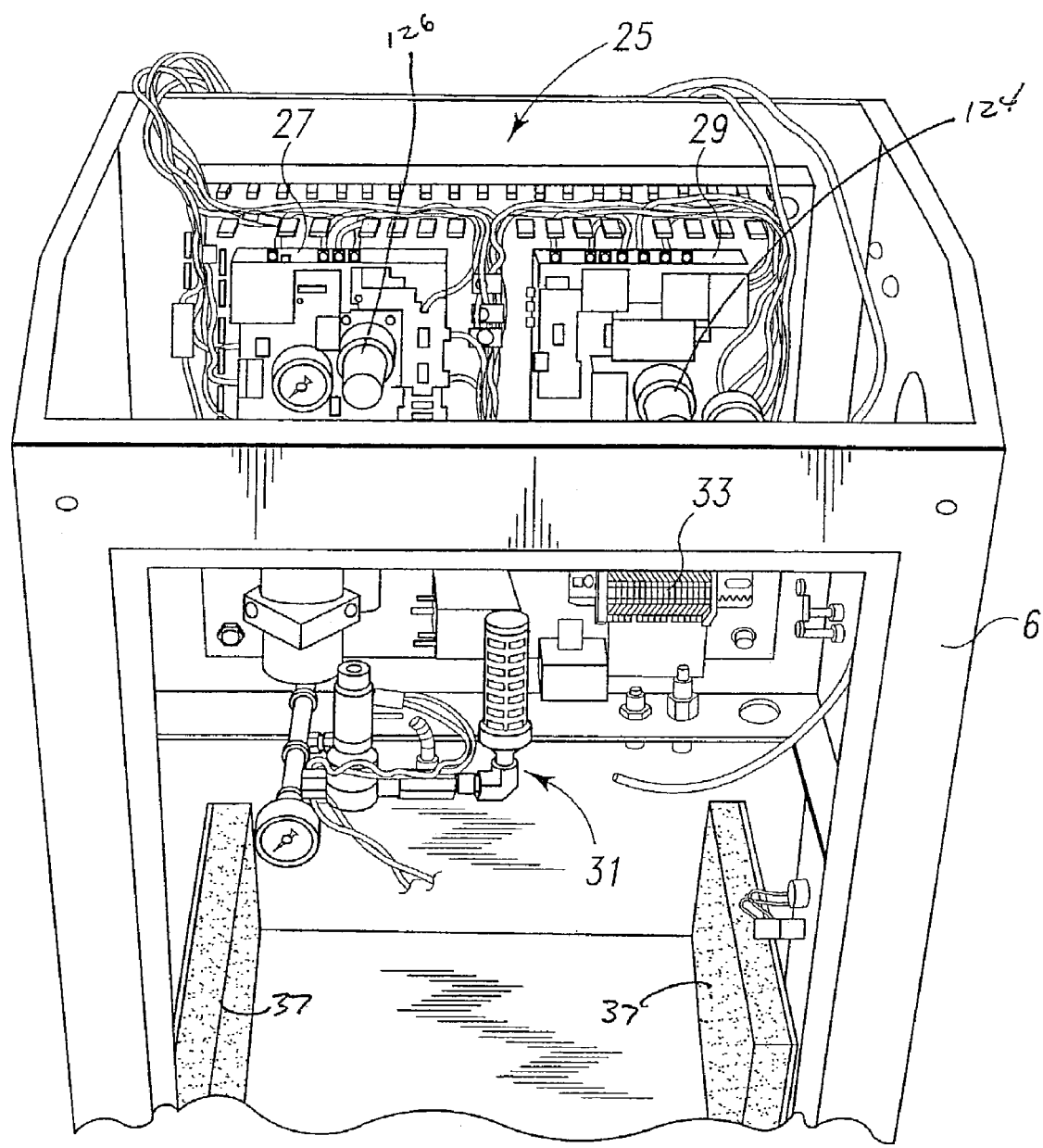
FIG. 9 is a view of the console showing the mounting panel mounted in the console, and showing the cavity in the lower portion which houses the compressor and vacuum.
Figure 10:
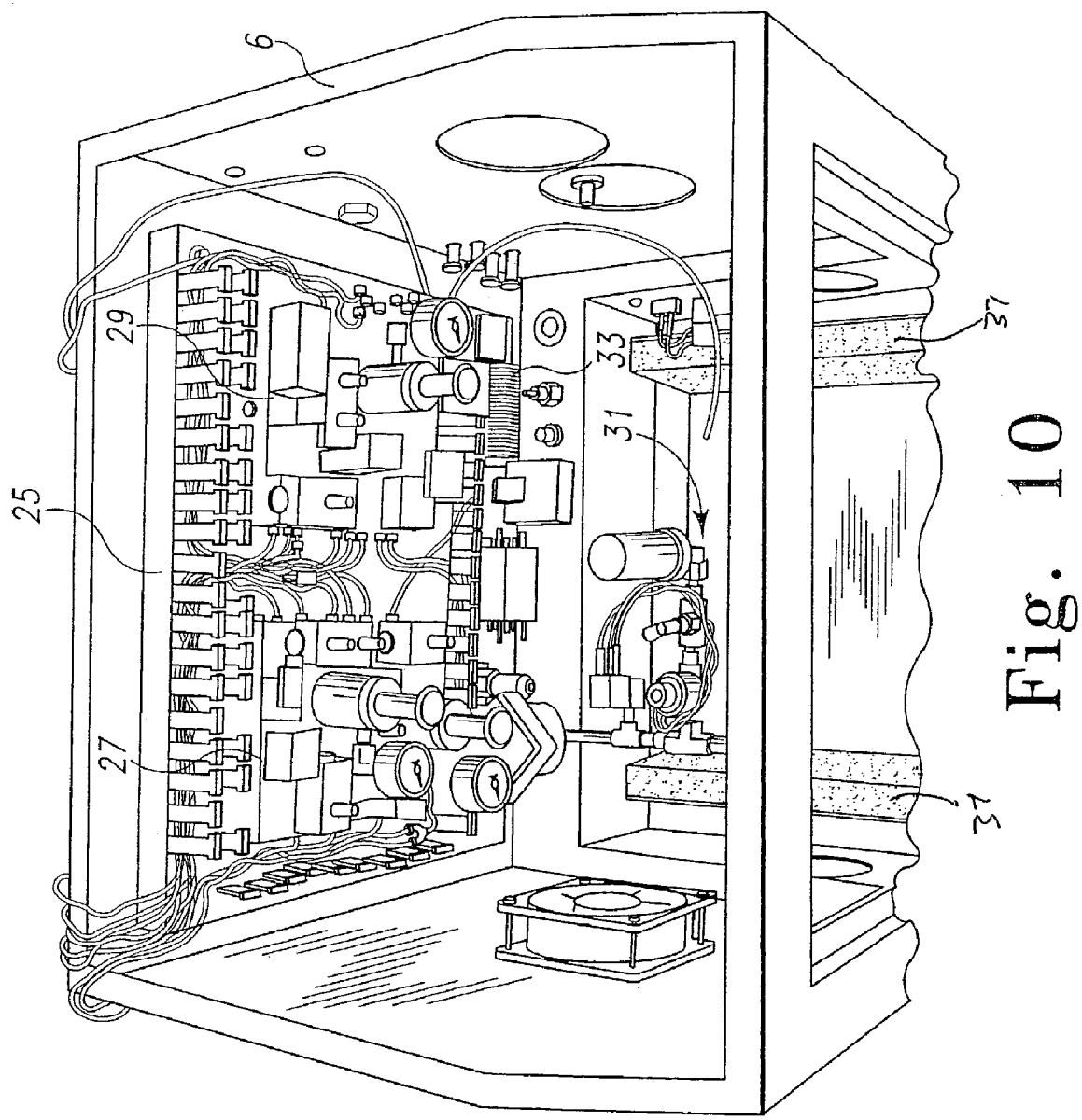
FIG. 10 is a view from the top of the console of FIG. 8.

FIG. 8 is a view of a console mounting panel 25 showing manifold subassemblies 27, 29, an evaporation subassembly 31, and a terminal block subassembly 33 mounted on the mounting panel 25. FIGS. 9 and 10 show the console mounting panel 25 mounted in the console 6. Compressor 11 and vacuum pump 19 are not installed in the illustrative FIGS. 9 and 10.

Figure 11:
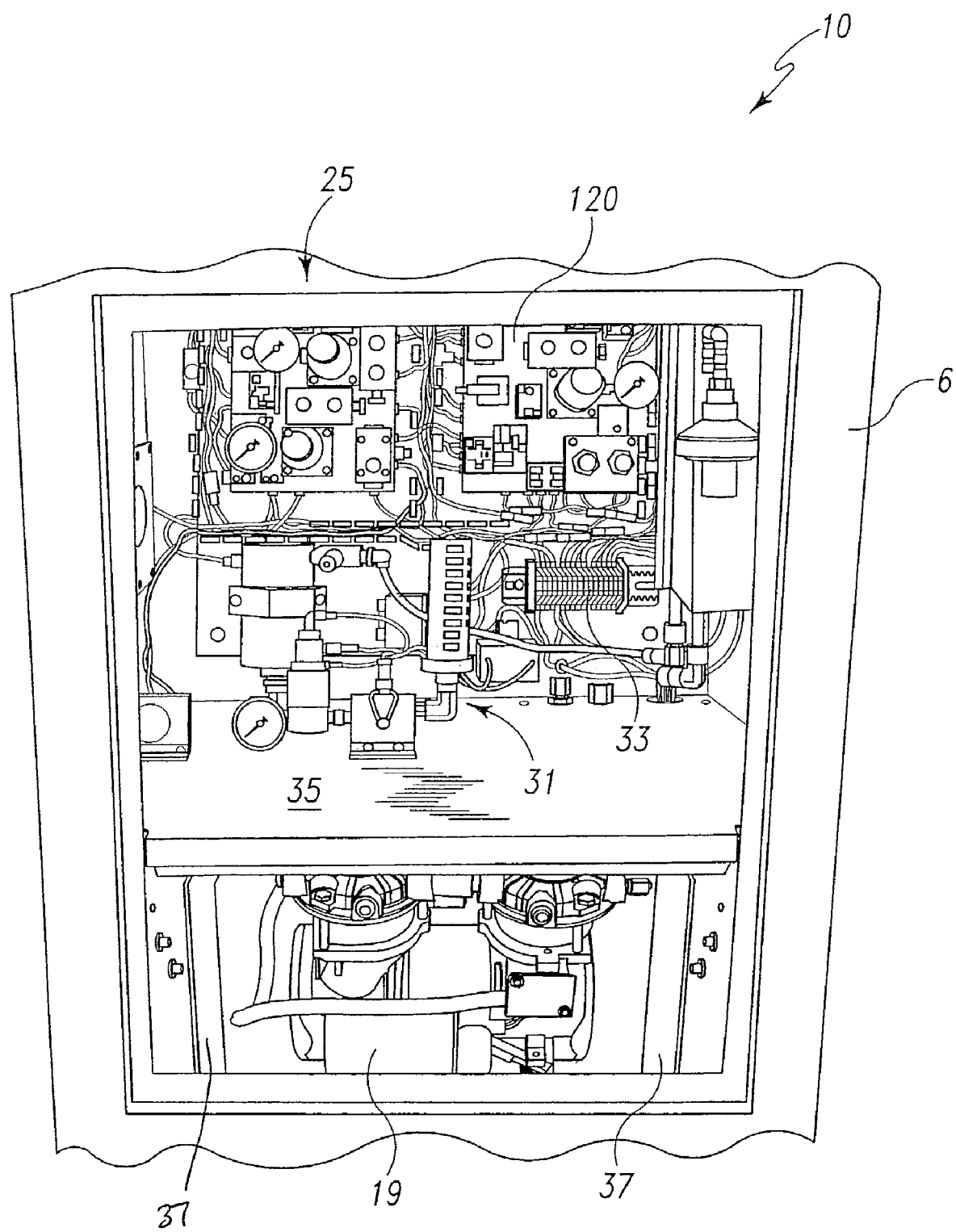
FIG. 11 is a view from the front of the open console similar to that of FIG. 9, showing the compressor and vacuum pump mounted in the lower portion of the console and showing other components of the pneumatic circuit mounted in the upper portion of the console.

Console 6 is shown in FIG. 11 to have compressor 11 and vacuum pump 19 mounted in the console 6 while other components of pneumatic circuit 10 including console mounting panel 25 are mounted in the upper portion of console 6. Shelf 35 is mounted to divide console mounting panel 25 from compressor 11 and vacuum pump 19. As noted above, soundproofing material 37 is positioned to surround compressor 11 and vacuum pump 19.

Figure 12A:
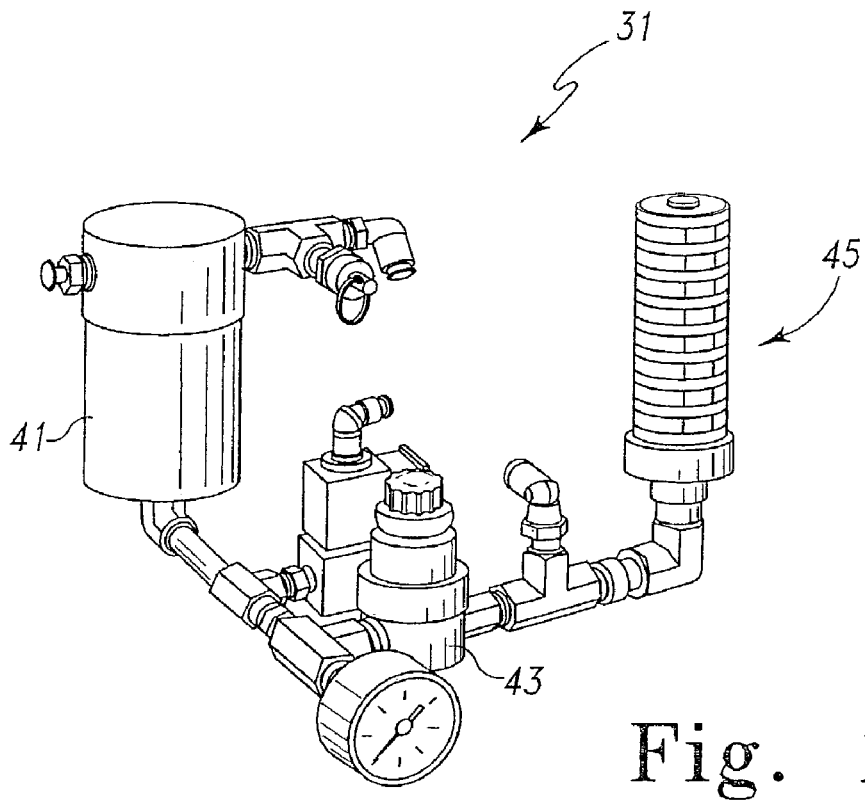
FIGS. 12A-B are views of two embodiments of a water evaporation subassembly.

FIG. 12A shows water evaporation subassembly 31 prior to installation in pneumatic circuit 10. Water evaporation subassembly 31 includes a filter 41, relief regulator 43, and gas-permeable absorber 45. Filter 41 is configured to direct condensation toward gas-permeable absorber 45, which in turn dissipates the condensation into the atmosphere. The schematic representation of water evaporation subassembly 31 can be seen in FIG. 17.

Figure 12B:
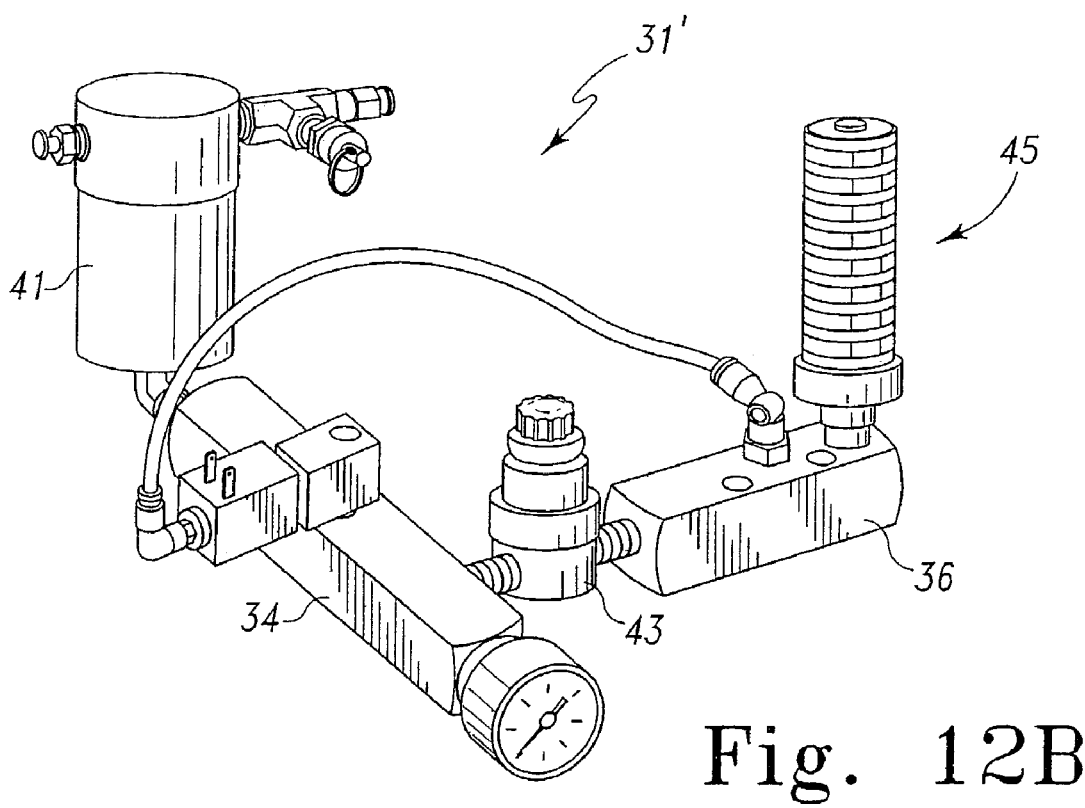

FIG. 12B is an alternative embodiment 31' of the water evaporation subassembly 31 of FIG. 12A. In alternative embodiment 31', conduits and fitting of subassembly 31 are replaced with manifolds 34, 36. Manifolds 34, 36 act as conduits and as fitting receivers for components such as filter 41, relief regulator 43, and gas-permeable absorber 45.

Figure 13B:
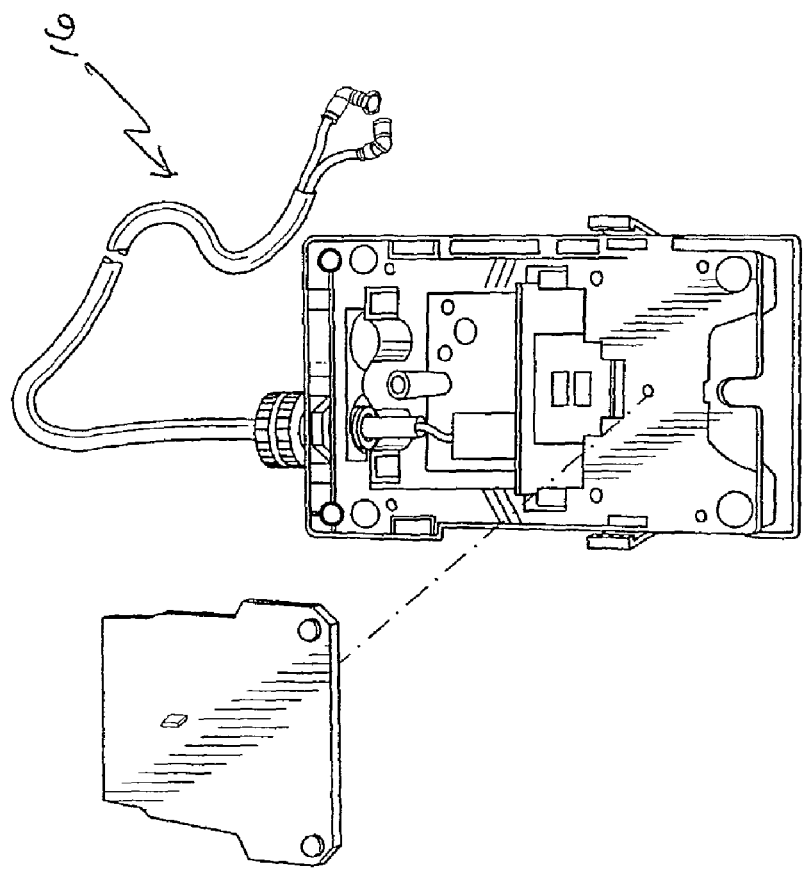
FIGS. 13A-B show, respectively, the foot switch prior to attachment of tubing, and the foot switch partially assembled after the attachment of tubing.
Figure 13A:
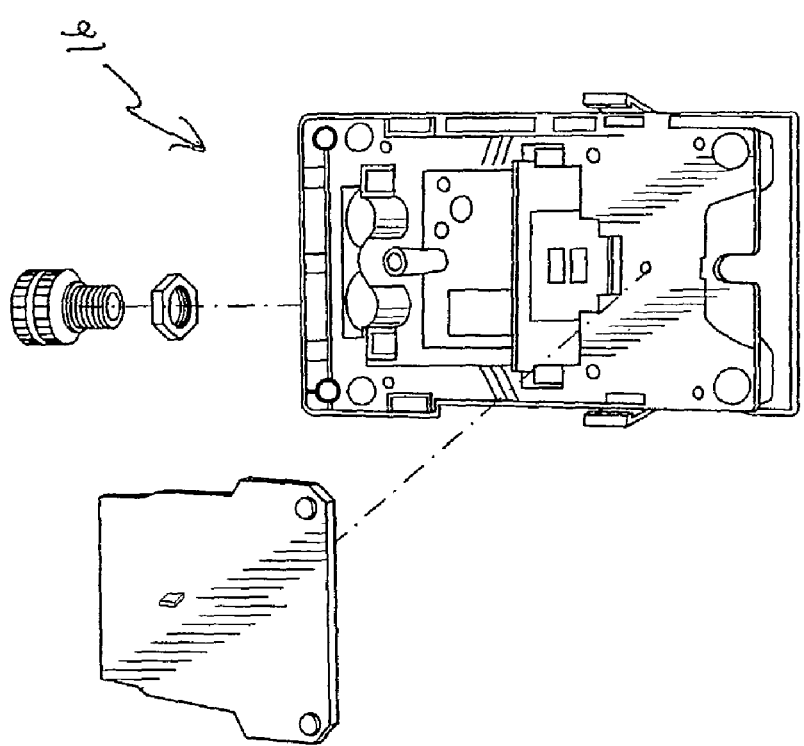

FIGS. 13A and 13B show the assembly of foot switch 16 prior to and after the attachment of tubing. FIG. 14 is a view of the terminal block subassembly 33 prior to installation on the console mounting panel 25, shown in FIG. 8. The terminal block subassembly 33 functions to distribute electrical power to the compressor 11, vacuum pump 19, and dump valves.

Custom designed manifolds 47, 49 can be seen in perspective view in FIGS. 15A-B. Manifolds 47, 49 are configured to route the pneumatic tubing (not shown in FIGS. 15A-B, but viewable in FIG. 8) within the console. Schematics for manifolds 47, 49 can be seen in FIGS. 20B and 21A-D.

Figure 16A:
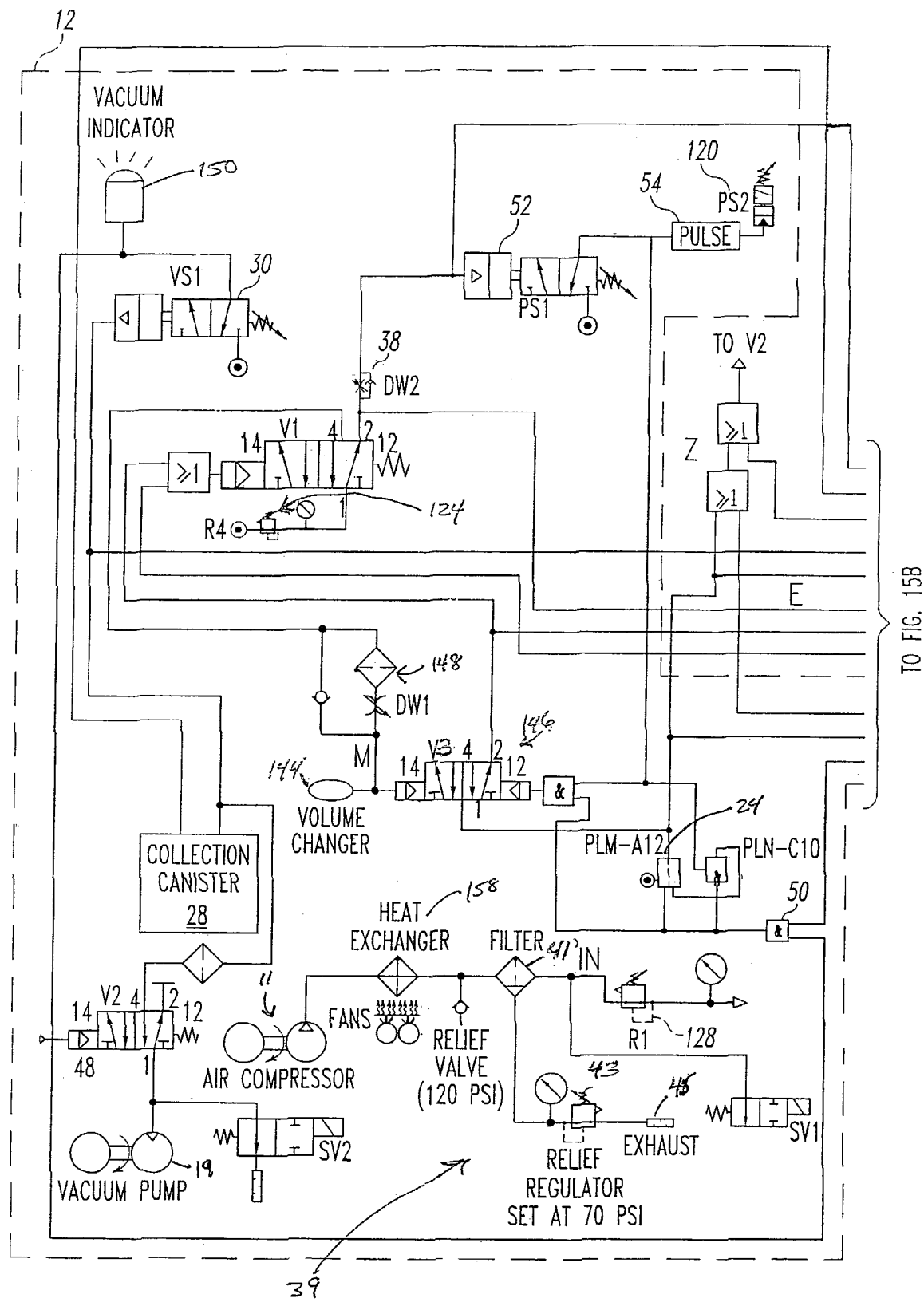
FIGS. 16A-B are schematic representations of the pneumatic circuit elements.
Figure 16B:
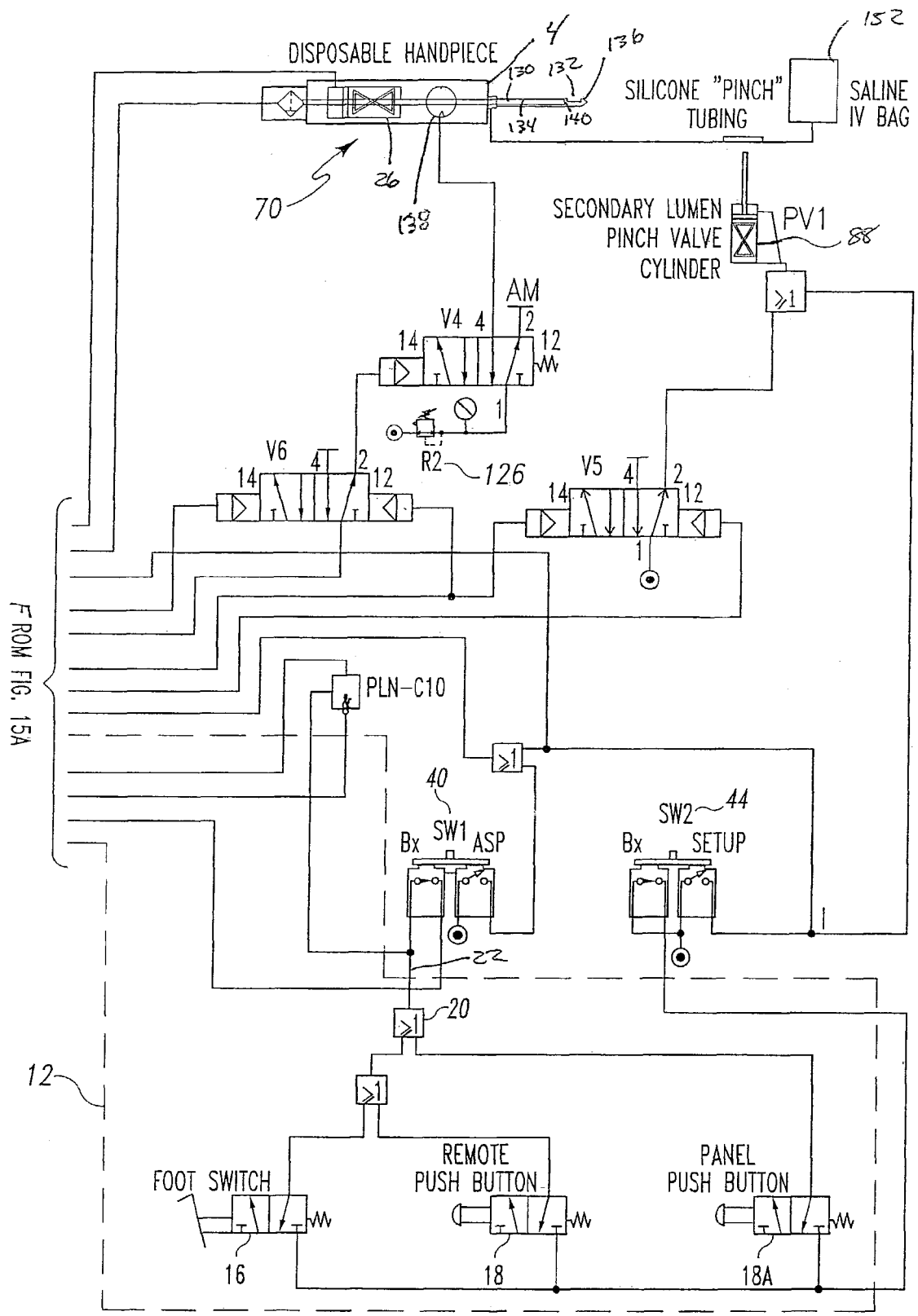

FIGS. 16A-B illustrate the schematic of the illustrative pneumatic circuit 10. Pneumatic circuit 10 includes a first sequence loop 12 (approximated as the elements within the broken lines) and a second sequence loop 14 (outside the broken lines). First sequence loop 12 is initiated with either a foot switch 16, a remote pushbutton 18, or a panel pushbutton 1 8A. Foot switch 16 is the illustrated embodiment in the drawings, however, any of the above foot switch 16, a remote pushbutton 18, or a panel pushbutton 18A, including combinations thereof, are within the scope of the disclosure.

Sensor 20 (shown in FIG. 16B) senses pressurization and permits passage of pressurized gas through path 22 when foot switch 16, pushbutton 18, or pushbutton 18A is actuated, or any combination thereof. The pressurized gas shifts the vacuum valve 48 (FIG. 16A), creating vacuum in collection canister 28. Vacuum sensor 30 passes a signal to the vacuum indicator 150 when the vacuum level reaches 20" Hg vacuum. Pressurized signals from components 30, 22 pass through the "and" gate 50 (FIG. 16A) and latch relay 24, which in turn signals cutter cylinder 26 to retract to a non-extended position. When cutter cylinder 26 is retracted into the non-extended position, pressurized gas is delivered to medical device 70, illustratively to operate pneumatic motor 138. However, it should be understood that pressurized gas may be utilized for any number of functions in a medical device, and is not restricted to the illustrative functions shown in hand wand 4.

A saline supply 152 (FIG. 16B) is also illustratively provided to medical device 70, the saline supply 152 fostering the flow of biological material removed by the medical device 70 to collection canister 28. Pinch valve 72, which includes pneumatically actuated stopper 88 (FIG. 16B), controls the flow of saline supply 152 in a manner described further herein.

Collection canister 28 collects biological material from the medical device 70 during the medical procedure using vacuum pressure. In addition to the biological material being collected, saline is collected in this manner. If the vacuum pressure fails, such failure is sensed by vacuum switch 30, and the cycle stops. Otherwise, pressurized gas continues to be delivered for a period of time determined by timing circuit 148.

Timing circuit 148 incorporates a restricted orifice that fills volume chamber 144 with gas and eventually signals valve 146 to turn on the pressurized gas to medical device 70. Pressurized gas causes cutter cylinder 26 to advance at a rate controlled by timing circuit 38 until it reaches the extended position (also the position held during insertion of the cannula of the illustrative medical device, described above). Such pressurized gas continues to build up in medical device 70 until pressure sensor 52 senses a predetermined gas pressure in cutter cylinder 26 and illustratively trips at approximately 24 psi, indicating the end of the stroke. At such a point, signaling device 54 causes a momentary audible signal, and also latch relay 24 resets, turning off device 70. If signal 22 is still present, the relay 24 will not reset and the process will automatically repeat. If the process repeats the audible tone has a shorter duration than if it resets.

It is also possible that cutter cylinder 26 does not fully advance to the extended position before pressure sensor 52 trips. In such an instance, cutter cylinder 26 may encounter difficulties cutting through the mass 142, and pressure will build up in cutter cylinder 26 even though the end of the stroke has not been reached. When the cylinder pressure reaches the predetermined amount of 24 psi, sensor 52 trips, regardless of the position of cutter cylinder 26 (and the attached cutter 134).

Setup switch 44 (FIG. 16B), which is controlled by knob 154 on control panel 9 (FIG. 1) allows an operator to load the saline tube into the pinch valve 72 and primes the medical device by actuating, in parallel, the retraction of cutter cylinder 26, the opening of saline pinch valve 72, and the opening of vacuum valve 48. During this setup mode, signals from 22 are ignored, thereby inhibiting a cycle start condition. Aspiration switch 40 (FIG. 16B), which is controlled by knob 156 on control panel 9 (FIG. 1) inhibits a cycle start condition and causes cylinder 26 to retract, if a signal delivered via path 22 is present the vacuum valve 48 shifts creating vacuum in the canister and the medical device.

Referring to FIGS. 16A-B, pneumatic circuit 10 operates in substantially the following fashion. Air compressor 11 is turned on and creates air pressure and flow. The compression process creates heat and condenses the humidity in the air. At such a point, condensed water is in gaseous state. The hot moist air is then passed through a fan-driven air-to-air heat exchanger 158 cooling the air and changing the water to a liquid state. The cooled air is then passed into a coalescing filter 41 where the water is captured in the filter media and drips into the bottom of the filter bowl. The filtered air then continues out to feed the control circuit.

The compressor runs continuously. If pressure is sensed by the relief regulator of greater than the set point of 70 psi, it will continuously vent the excess pressure. If the system is on and not in cycle, 99% of the compressor flow rate will vent out of the relief regulator. While the system is cycling the medical device, approximately 40% of the system capability will continuously flow through the relief regulator.

The water that is collected in the bottom of the filter bowl is dissipated with water evaporation subassembly 39. Water passes from the filter 41 through the relief regulator 43 and into the base of the permeable exhaust member 45. The exhaust member 45 acts as a wick, drawing the fluid up the media. The flow rate through the exhaust member 45 and the large "wick" surface area cause the liquid water to evaporate into a gas state. The flow rate through the enclosure caused by the heat exchanger fans removes the water vapor from the cabinet, thus eliminating the need to collect water and drain it from the system. Illustratively, a filter "muffler" is used as a permeable exhaust member 45, the muffler being available from Allied Witan Company, of Cleveland, Ohio, as part number F02.

The pneumatic circuit components are mounted to custom aluminum manifolds 47, 49 minimizing the use of fittings and keeping the system compact. The components are "sub-base" style versions of the component allowing for ease of replacement. Each component that needs adjusted is bench tested and set to the specified level using certified fixtures. Diagrammatic representations of the manifolds can be seen in FIGS. 21A-D.

Console 6 is designed to isolate the noise and heat created by compressor 11 and vacuum pump 19. Design specifications for console 6 can be seen in FIGS. 19A-D. Shelf 35 divides the cabinet into two sections. The lower section contains the spring-mounted pumps 11, 19, soundproofing material 37, and fans to isolate vibration, heat, and noise, as can be seen in FIG. 7.

Figure 22A:
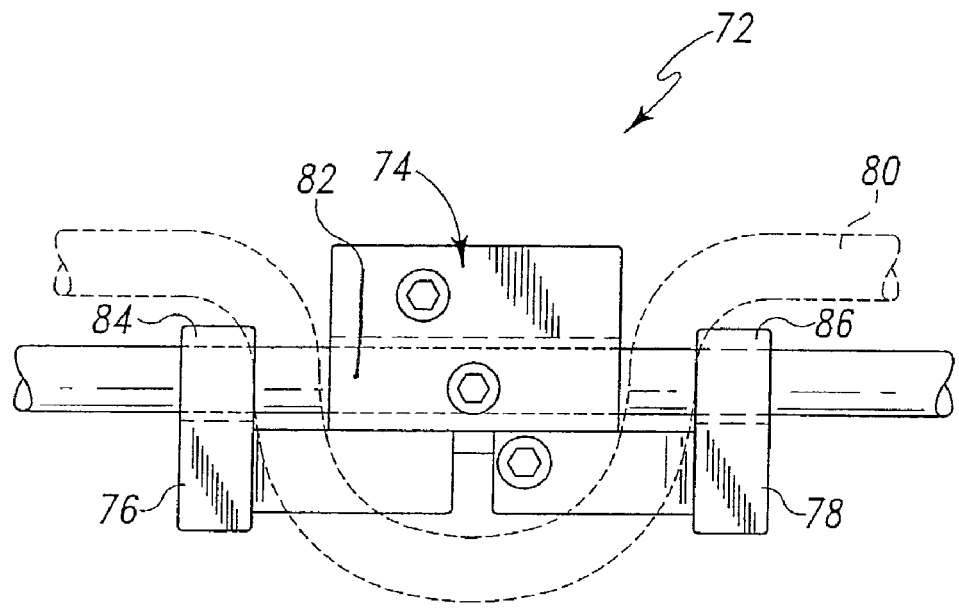
FIG. 22A shows a top view of a pinch valve configured to control the flow of saline.
Figure 22B:
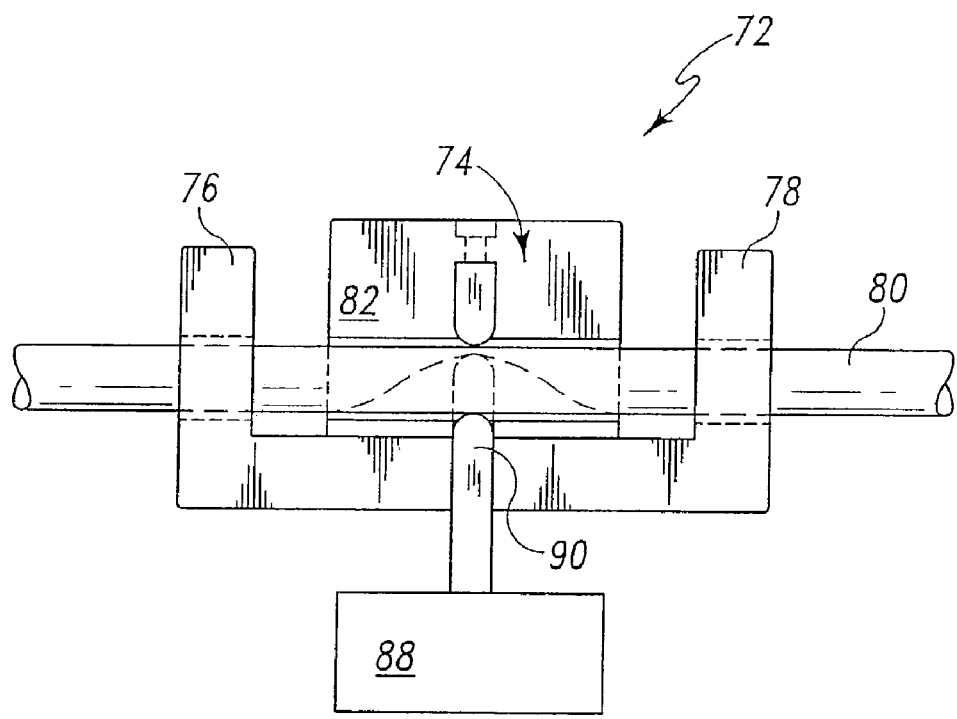
FIG. 22B is a front elevation view of the pinch valve shown in FIG. 22A, showing the tube positioned in the pinch valve, and showing the movement of the plunger between a flow position and a non-flow position.
Figure 23A:
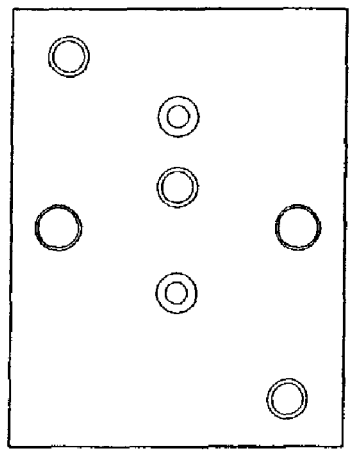
FIGS. 23A-D show specification drawings for the gasket.
Figure 23B:
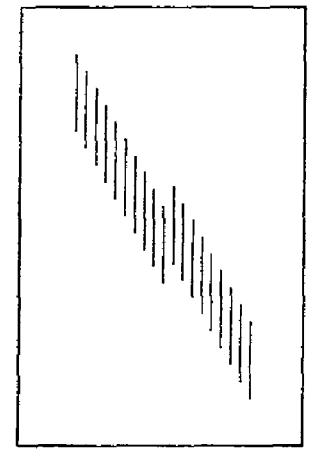
Figure 23C:
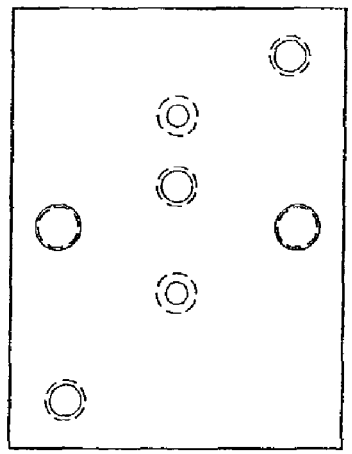
Figure 23D:
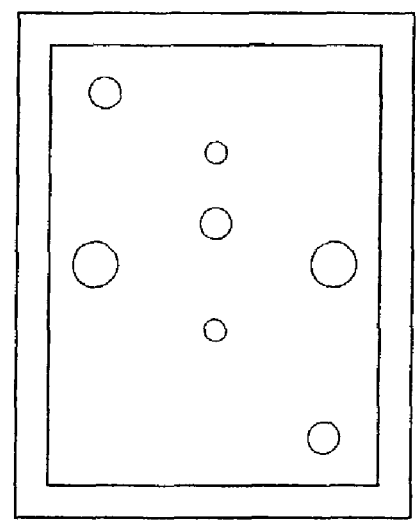
Figure 24A:
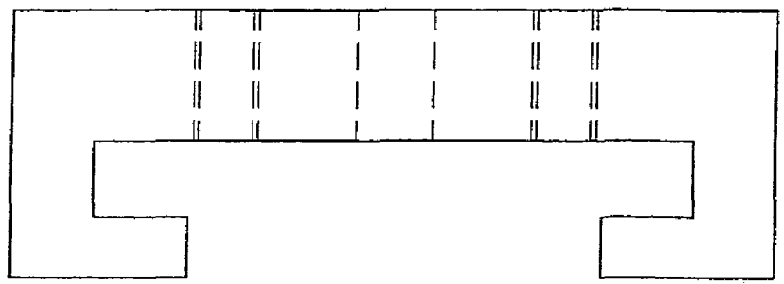
FIGS. 24A-B show a top view and a front elevation view, respectively, of a canister bracket.
Figure 24B:
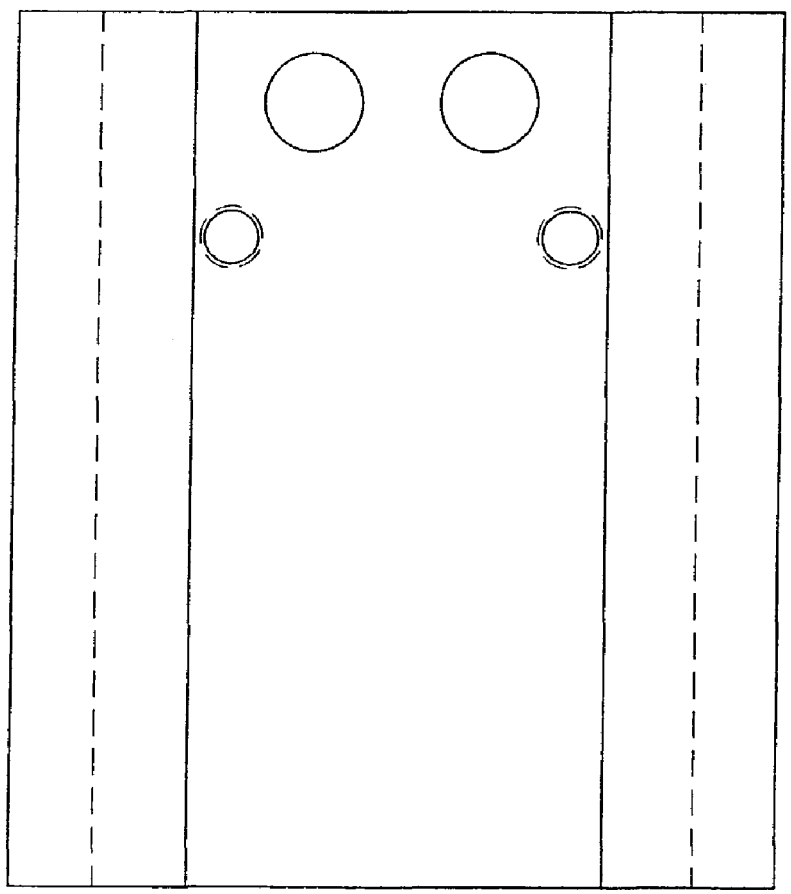
Figure 25B:
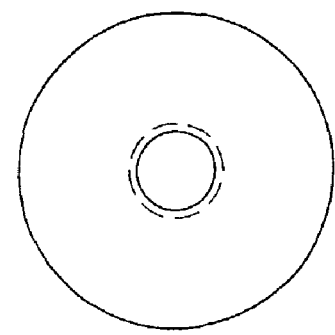
FIGS. 25A-D show front and side views of a pair of hose wrap pins.
Figure 25D:
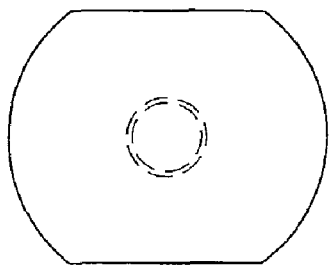
Figure 25A:
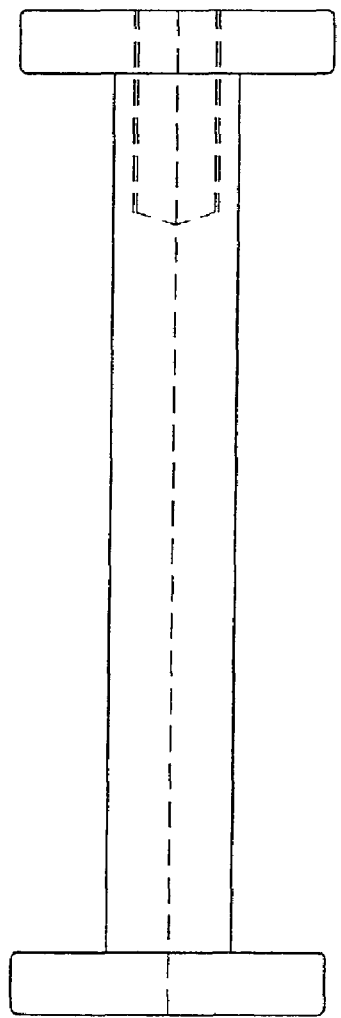
Figure 25C:
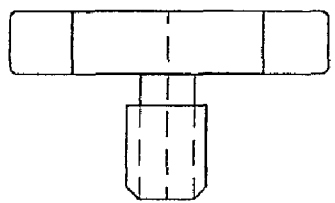

As shown in various views in FIGS. 22A-B, pinch valve 72 includes a retainer comprised of a central catch 74 and opposing catches 76, 78. See also a view of pinch valve 72 in FIG. 1. Silicone tubing 80 is bent into a configuration as shown in broken lines, and pushed between central catch 74 and opposing catches 76, 78. When pulled taut, silicone tubing 80 assumes a substantially straight configuration and is disposed under cantilevered portion 82 of central catch 74, and cantilevered portions 84, 86 of opposing catches 76, 78 respectively, as shown in FIG. 22A. Such a configuration secures the silicone tubing 80 and prevents accidental removal of silicone tubing 80 from pinch valve 72.

Pneumatically actuated stopper 88, shown diagrammatically in FIG. 22B, moves a piston 90 between a stopped position (shown in broken lines) and a flow position. The default position is the stopped position, stopping the flow of fluid through the silicone tubing 80.

Figure 26A:
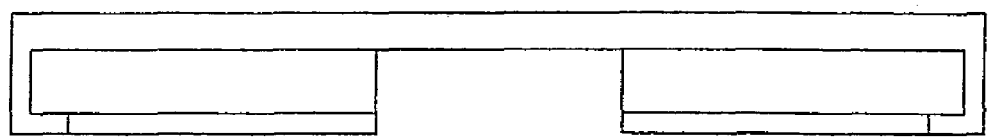
FIGS. 26A-B show a foot switch holder.
Figure 26B:
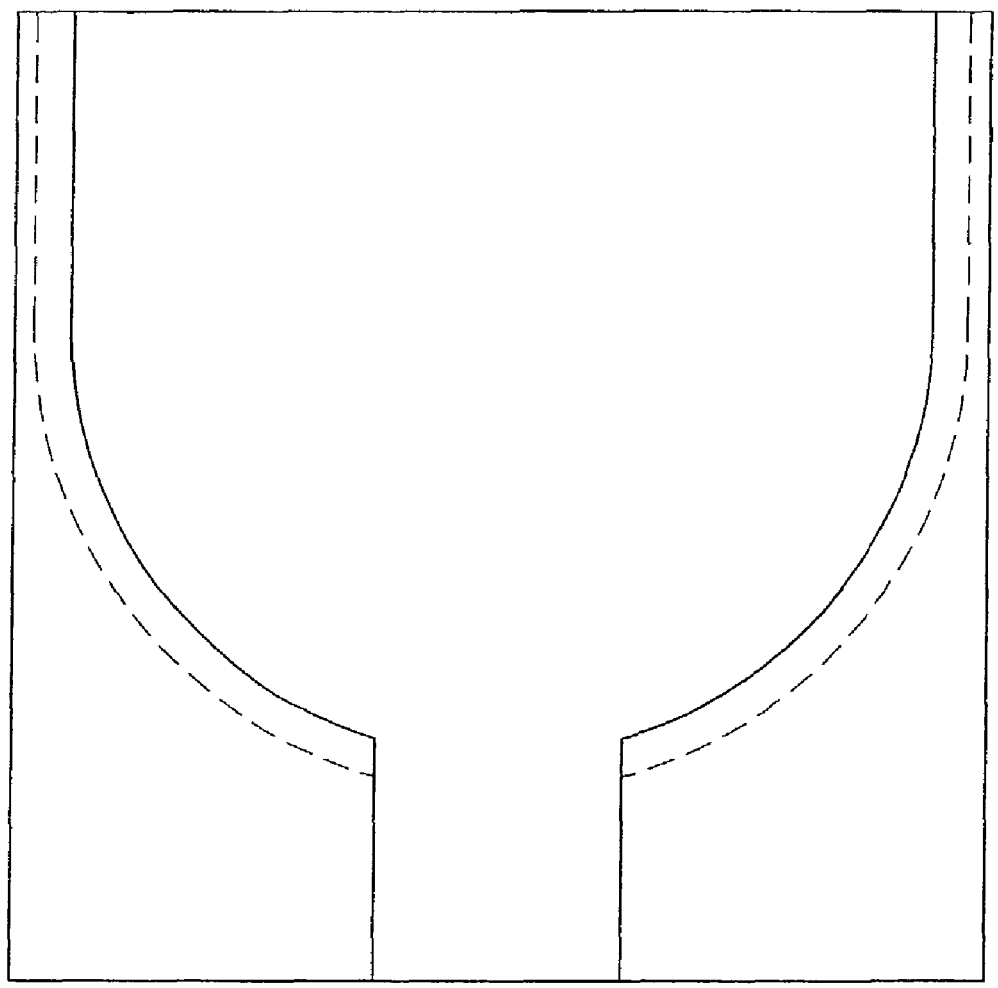
Figure 27:
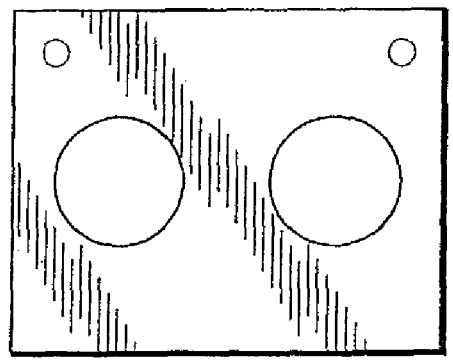
FIG. 27 shows a valve bracket.
Figure 28A:
FIGS. 28A-B show an embodiment of tie-down rails.
Figure 28B:
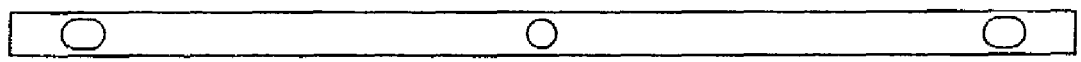

FIGS. 25A-D show a pair of hose wrap pins that is used to wrap the foot switch tube set and the power cord when the system is not in use. FIGS. 26A-B show a foot switch holder. FIG. 27 shows a valve bracket. And FIGS. 28A-B show an embodiment of tie-down rails.

Figure 29:
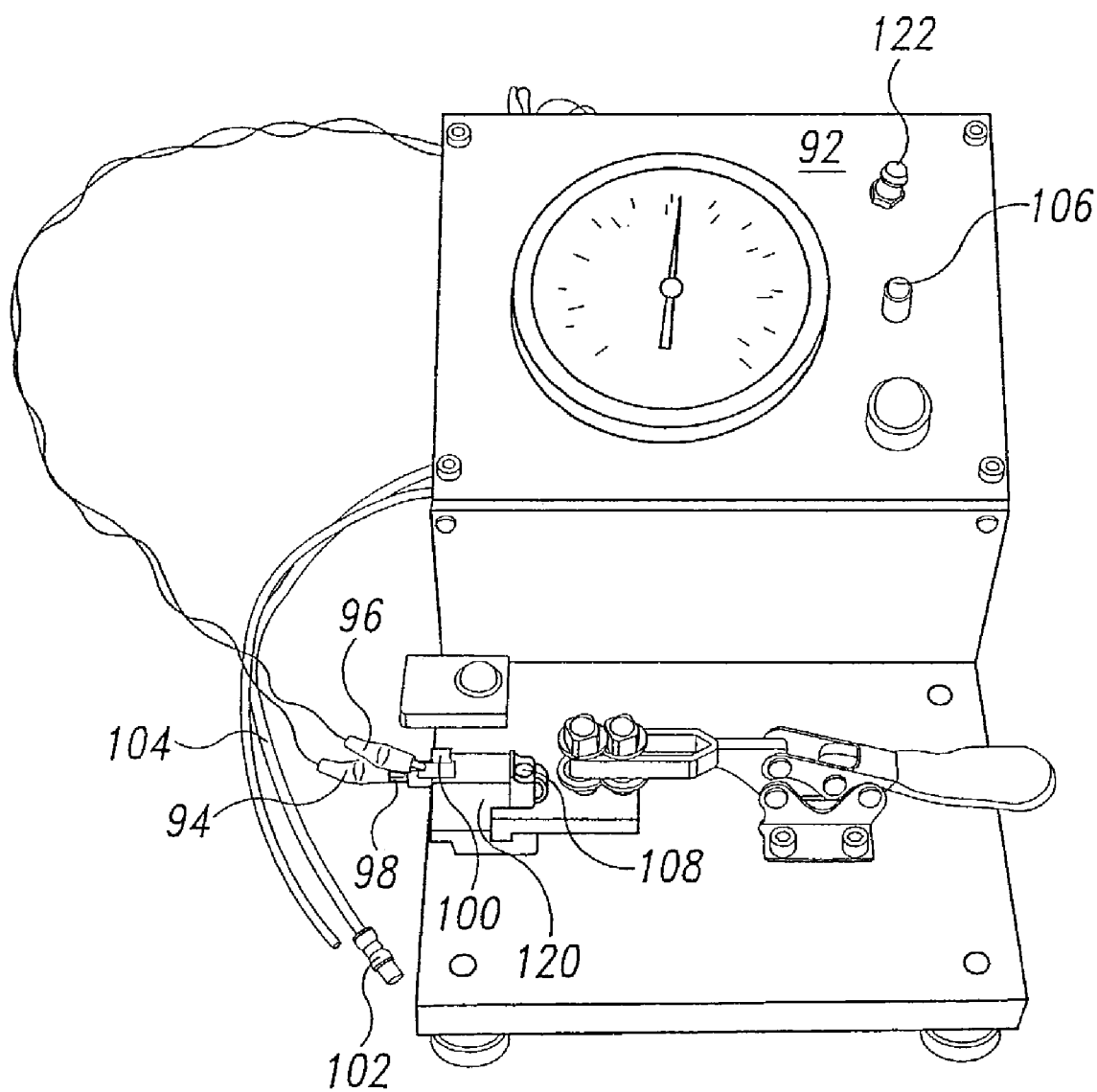
FIGS. 29-33 show the test equipment used in testing certain elements in the pneumatic circuit in various stages of the test.

The test module 92 for testing Airtrol electric pressure switch 120 (as shown in FIGS. 11 and 16A), model number F-4200-60-MM, can be seen in FIGS. 29-33. The switch 120 is placed on test module 92 and clamped in place, as seen in FIG. 29. A red jumper 94 is connected to the normally open (N.O.) terminal 98 of switch 120. Black jumper 96 is connected to COM terminal 100. A plugged union fitting 102 is connected to an end of natural colored tube 104. With an air supply to test module 92 turned on, 2-position detented button 122 is pulled out and pressure observed. It is further observed when green indicator light 106 turns on. If green indicator light 106 does not turn on at 20 psi +/−0.5 psi, then button 122 should be pushed back in and adjustments made to switch 120, and testing done again. After the proper target pressure is obtained, a green dot sticker 108 is placed over the adjustment screw. Pneumatic vacuum switch VP-701-30-MM is tested in a similar fashion, with a targeted setting of 20" Hg vacuum.

Figure 30:
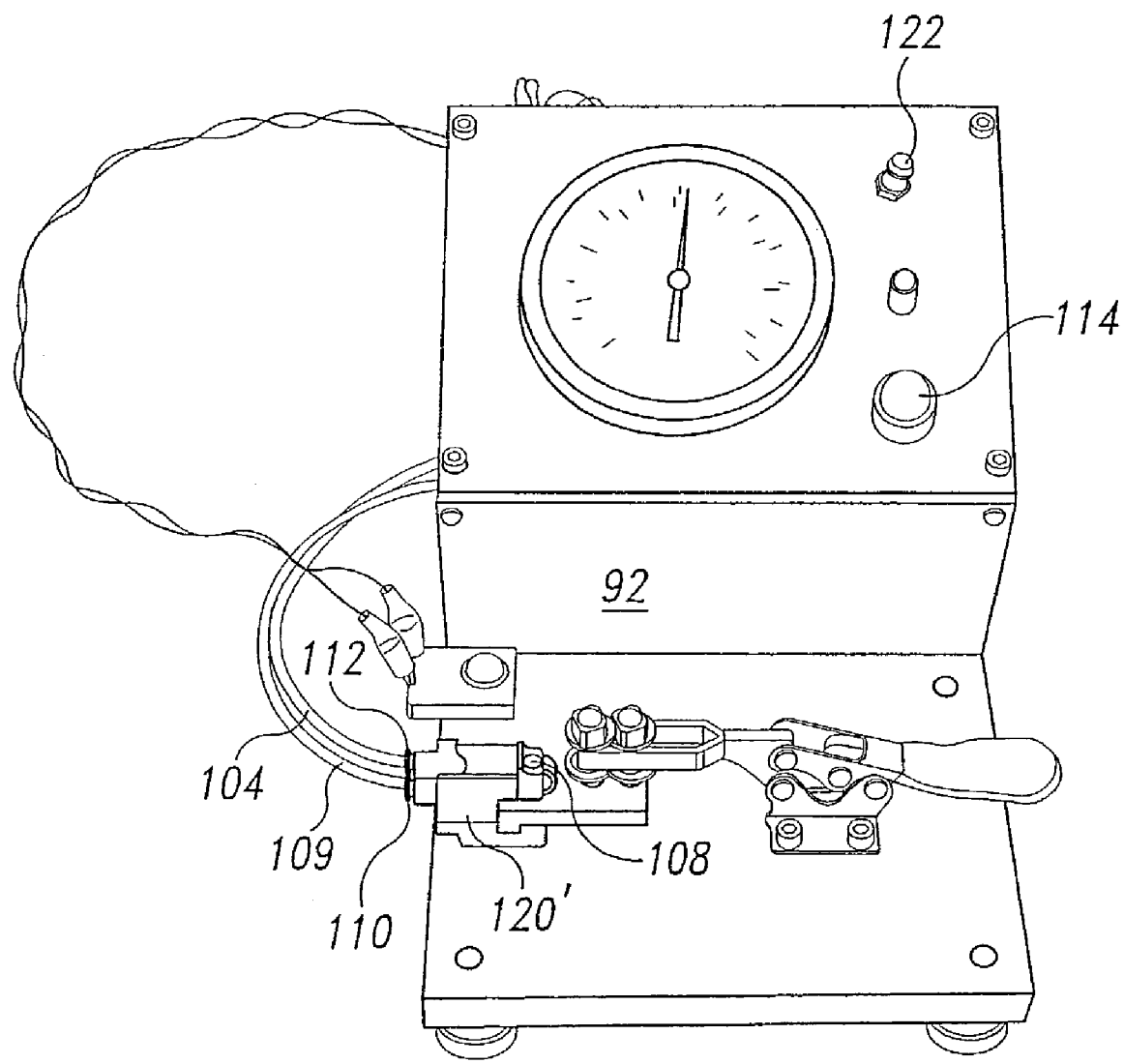
Figure 31:
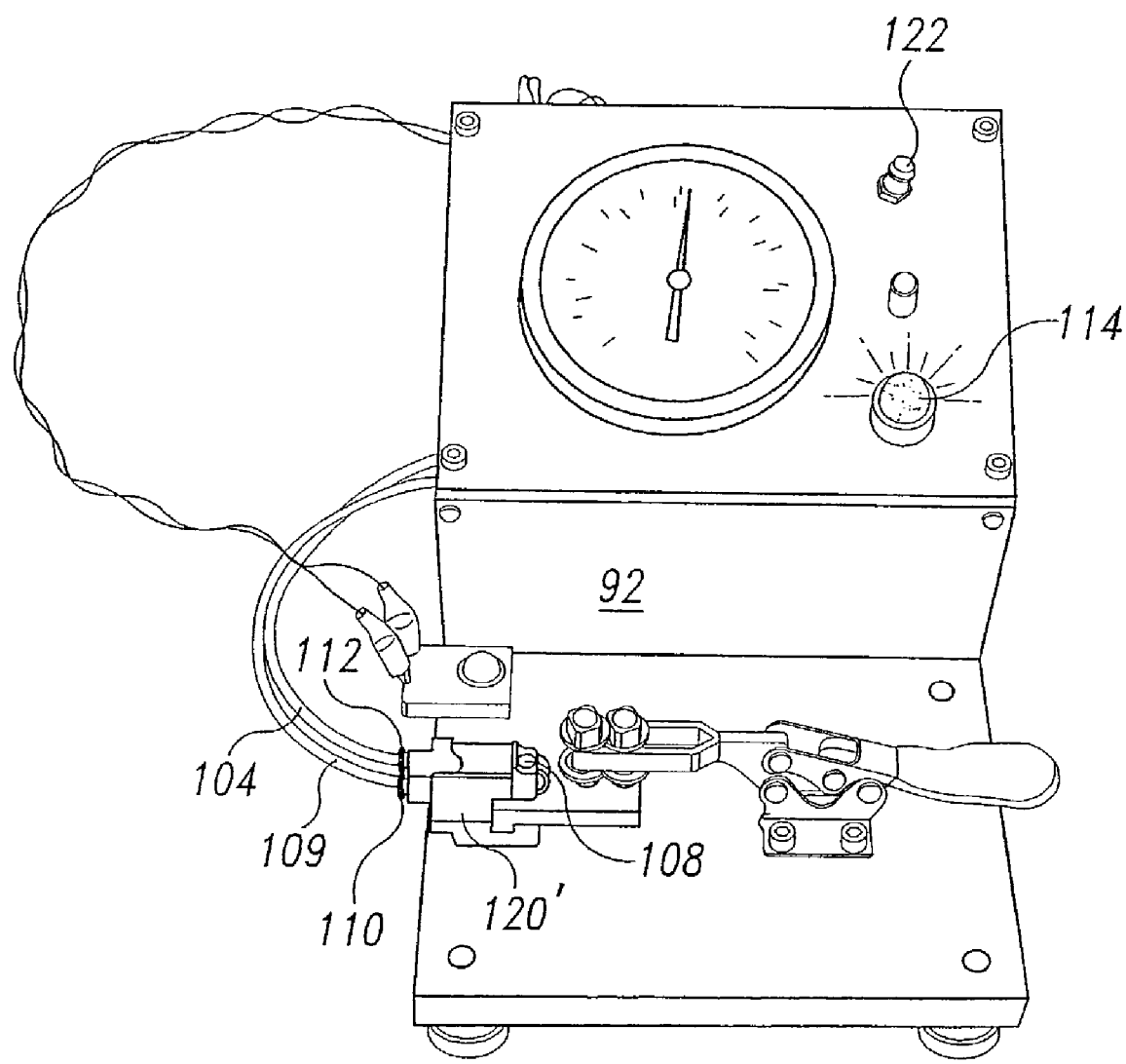

Another test procedure for test module 92 is shown in FIGS. 30 and 31. In such a procedure, Airtrol pneumatic pressure switch 120' (model number PP-701-30-MM) is tested. Red tube 109 is connected to output port 110. Natural tube 104 is connected to input port 112. With an air supply to test module 92 turned on, button 122 is pulled out and pressure at which large green light 114 comes on is observed. If large green light 114 does not turn on at 24 psi +/−0.5 psi, then button 122 should be pushed back in and adjustments made to switch 120', and testing done again. After the proper target pressure is obtained, a green dot sticker 108 is placed over the adjustment screw.

Figure 32:
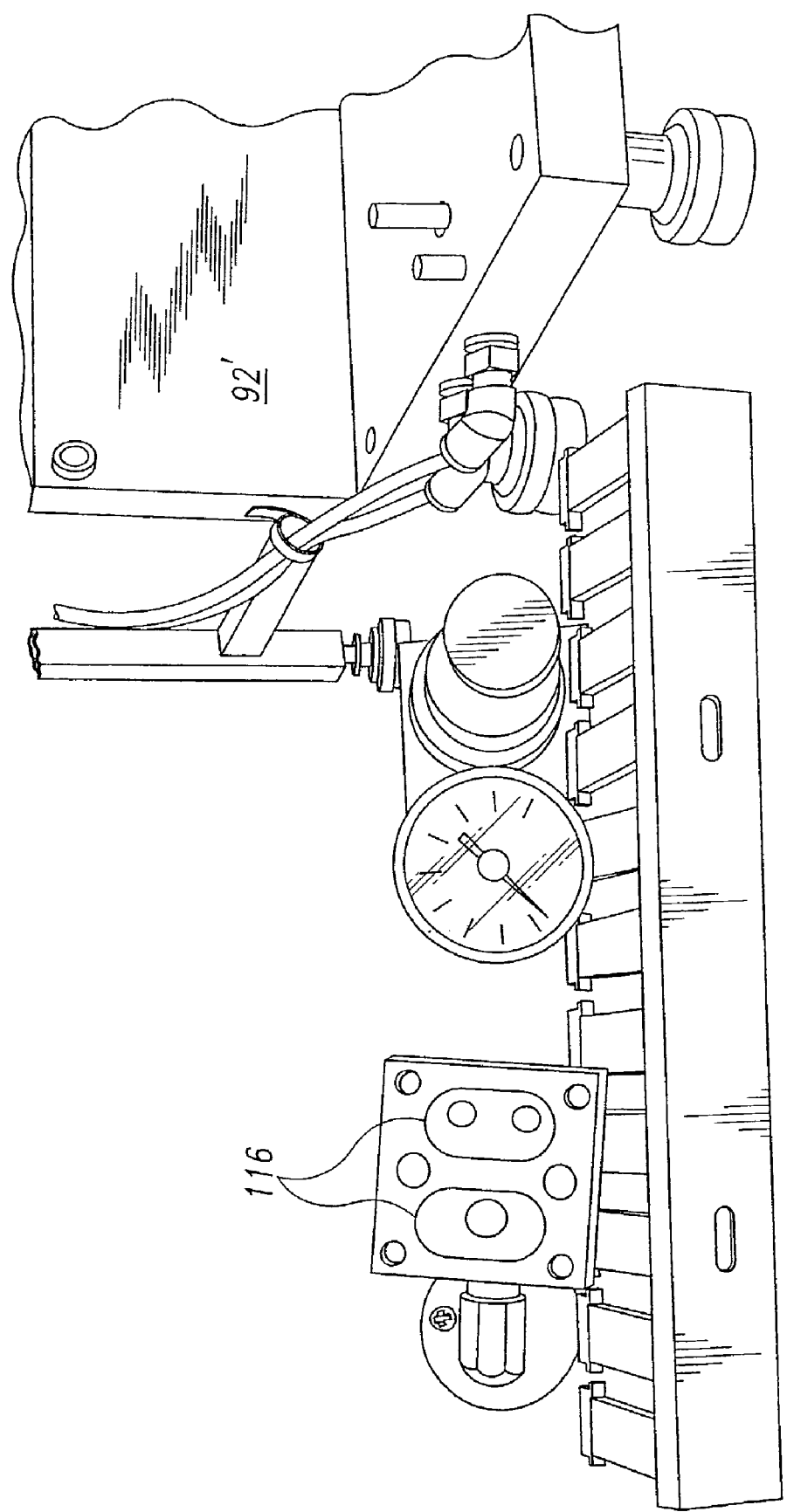
Figure 33:
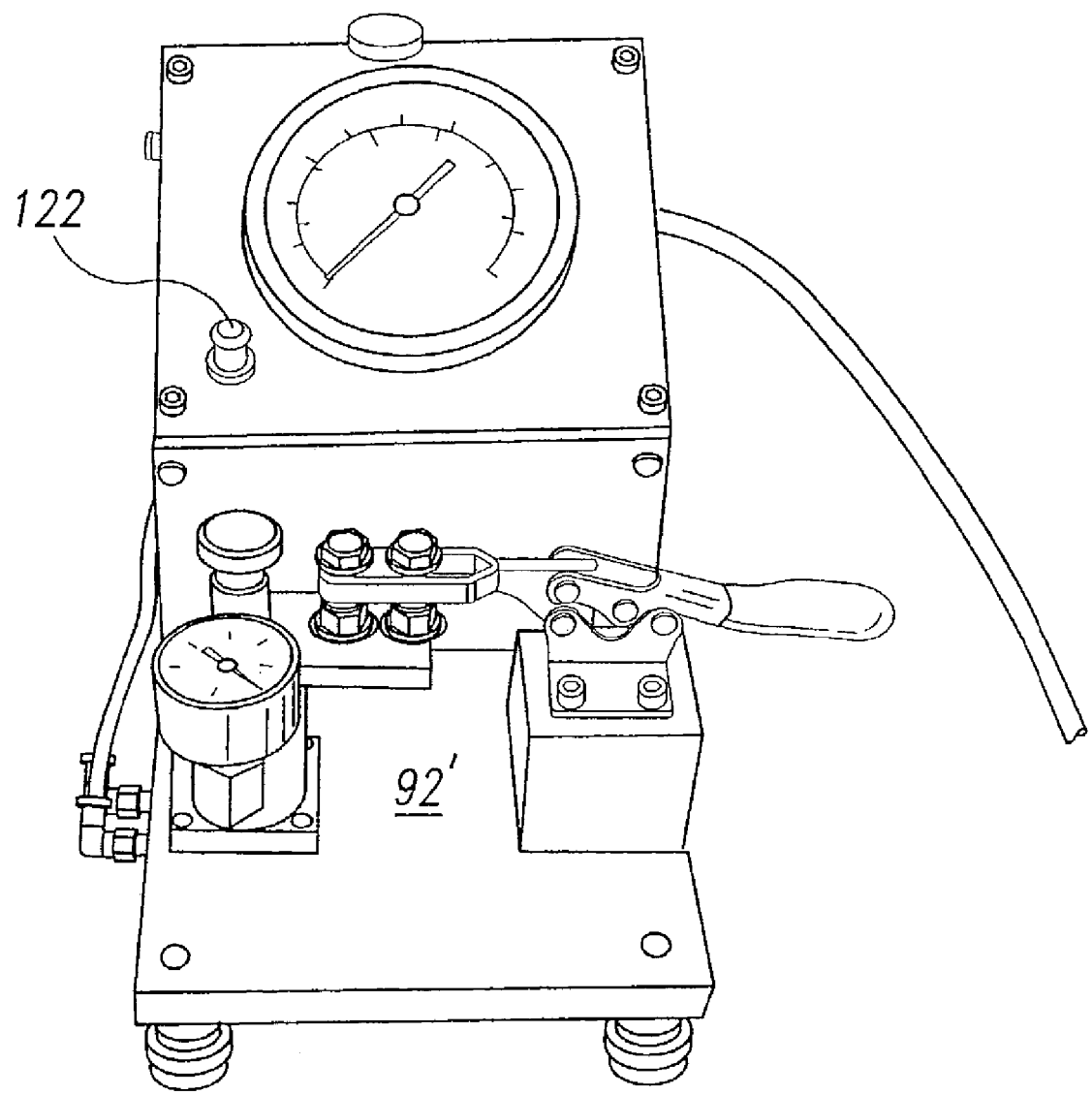

Yet another test module 92' for testing various regulators is shown in FIGS. 32 and 33. This test module 92' is illustratively used for the cutter cylinder regulator 124 (model R4, R01-10 w/60 psi gauge), the air motor regulator 126 (model R2, R01-12 w/60 psi gauge), and the main regulator 128 (model R1, R01-12 w/160 psi gauge). The regulators are illustrated schematically in FIGS. 16A-B, and on diagrammatic views of the manifolds in FIGS. 20B and 21A-B. During testing, the tested regulator 124, 126, 128 should be set for the appropriate target pressure (60 psi, 60 psi, and 160 psi, respectively). Next, two O-rings 116 (seen in FIG. 32) should be installed in the bottom of the tested regulator. The regulator 124, 126, 128 is then placed on the test module 92' aligning the locating pin and locating hole found on the test module and regulator. Regulator 124, 126, 128 is then clamped in place.

Target pressures during testing of regulators 124, 126, 128 varies depending on the regulator. Model R4 is targeted for 30 psi, rising. Model R2 is targeted for 40 psi, rising. Model R1 is targeted for 60 psi, rising. Once pressure is dialed in to the appropriate target, the regulator nut is tightened to prevent knob movement and a permanent marker is used to mark the cannula position of the regulator gauge. Finally, a green dot is placed in the center of the gauge face.

Illustrative parts used in the production of the above-described embodiment can be found in FIGS. 34A-C. It should be understood, however, that other parts and constructions are within the scope of the disclosure.

While the disclosure is susceptible to various modifications and alternative forms, specific exemplary embodiments thereof have been shown by way of example in the drawings and have herein been described in detail. It should be understood, however, that there is no intent to limit the disclosure to the particular forms disclosed, but on the contrary, the intention is to cover all modifications, equivalents, and alternatives falling within the spirit and scope of the disclosure as defined by the appended claims.

A plurality of advantages arises from the various features of the present disclosure. It will be noted that alternative embodiments of various components of the disclosure may not include all of the features described yet still benefit from at least some of the advantages of such features. Those of ordinary skill in the art may readily devise their own implementations of a pneumatic circuit that incorporate one or more of the features of the present disclosure and fall within the spirit and scope of the disclosure.

The invention claimed is:

1. A biopsy device comprising: a cannula with an orifice, the cannula being configured for insertion into a body to a point such that the orifice is adjacent to a tissue mass to be biopsied; and a six-vane pneumatic rotary motor capable of continual rotation, the rotary motor having a hollow shaft disposed within the cannula, the pneumatic motor shaft having a cutter end configured to rotate relative to the orifice to selectively cut tissue from the mass; wherein the tissue cut from the mass is drawn through the hollow shaft and through the pneumatic rotary motor during operation of the biopsy device.

2. The biopsy device of claim 1, wherein the cannula defines an axis and the cutter end, the pneumatic rotary motor shaft, and the cannula are coaxially aligned.

3. The biopsy device of claim 2, wherein the cutter rotates about the axis.

4. The biopsy device of claim 1, further comprising a pneumatic circuit coupled to the rotary pneumatic motor, the pneumatic circuit providing suction to the shaft for drawing the cut tissue through the shaft.

5. The biopsy device of claim 4, wherein the pneumatic circuit is further configured to provide compressed air to the pneumatic rotary motor.

6. The biopsy device of claim 1, further comprising a pneumatic switch configured to permit an operator to selectively operate the pneumatic rotary motor by actuating the pneumatic switch.

7. The biopsy device of claim 1, wherein the biopsy device is substantially free of magnetically sensitive objects such that it can be operated in conjunction with a Magnetic Resonance Imaging device.

8. A medical device comprising: a biopsy device having a six-vane rotary motor, the biopsy device being configured to selectively cut tissue from a body during a cutting cycle; a pneumatic circuit coupled to the biopsy device for controlling the operation of the biopsy device; and a switch for activating the cutting cycle of the biopsy device, the switch and biopsy device being composed of substantially non-magnetic materials such that the biopsy device may be operated in conjunction with a Magnetic Resonance Imaging device.

9. The medical device of claim 8, wherein the biopsy device comprises a pneumatic motor.

10. A medical device comprising: a biopsy device having a six-vane rotary motor, the biopsy device being configured to selectively cut tissue from a body; a pneumatic circuit coupled to the biopsy device for controlling the operation of a rotary motor housed in the biopsy device; a housing for the pneumatic circuit; a vacuum port coupled to the housing and having a vacuum conduit leading to the biopsy device; and a compressed air port coupled to the housing and having a compressed air conduit leading to the biopsy device.

11. The medical device of claim 10, further comprising a pinch valve coupled to the housing, the pinch valve being configured to control pneumatic flow through the vacuum conduit.

12. The medical device of claim 10, further comprising an indicator coupled to the housing, the indicator signaling when the pneumatic circuit is operational to control the biopsy device.

13. The medical device of claim 12, wherein the indicator is pneumatically controlled by the pneumatic circuit.

* * * * *

(12) INTER PARTES REEXAMINATION CERTIFICATE (651st)
United States Patent
Schwindt

(10) Number: US 7,749,172 C1
(45) Certificate Issued: Jul. 23, 2013

(54) PNEUMATIC CIRCUIT

(75) Inventor: Jeffrey Schwindt, Indianapolis, IN (US)

(73) Assignee: Tissue Extraction Devices, LLC, Indianapolis, IN (US)

Reexamination Request:
No. 95/001,743, Sep. 6, 2011

Reexamination Certificate for:
Patent No.: 7,749,172
Issued: Jul. 6, 2010
Appl. No.: 10/461,315
Filed: Jun. 13, 2003

Related U.S. Application Data

(63) Continuation of application No. 10/420,197, filed on Apr. 22, 2003, now abandoned.

(60) Provisional application No. 60/374,952, filed on Apr. 23, 2002.

(51) Int. Cl.
*A61B 10/00* (2006.01)
*A61B 17/32* (2006.01)

(52) U.S. Cl.
USPC .................. 600/566; 600/567; 606/167

(58) Field of Classification Search
None
See application file for complete search history.

(56) References Cited

To view the complete listing of prior art documents cited during the proceeding for Reexamination Control Number 95/001,743, please refer to the USPTO's public Patent Application Information Retrieval (PAIR) system under the Display References tab.

*Primary Examiner* — William C. Doerrler

(57) ABSTRACT

A pneumatic circuit and other components are provided for the operation of a medical device. The pneumatic circuit provides controlled pressurized air to a medical device for use during a medical procedure.

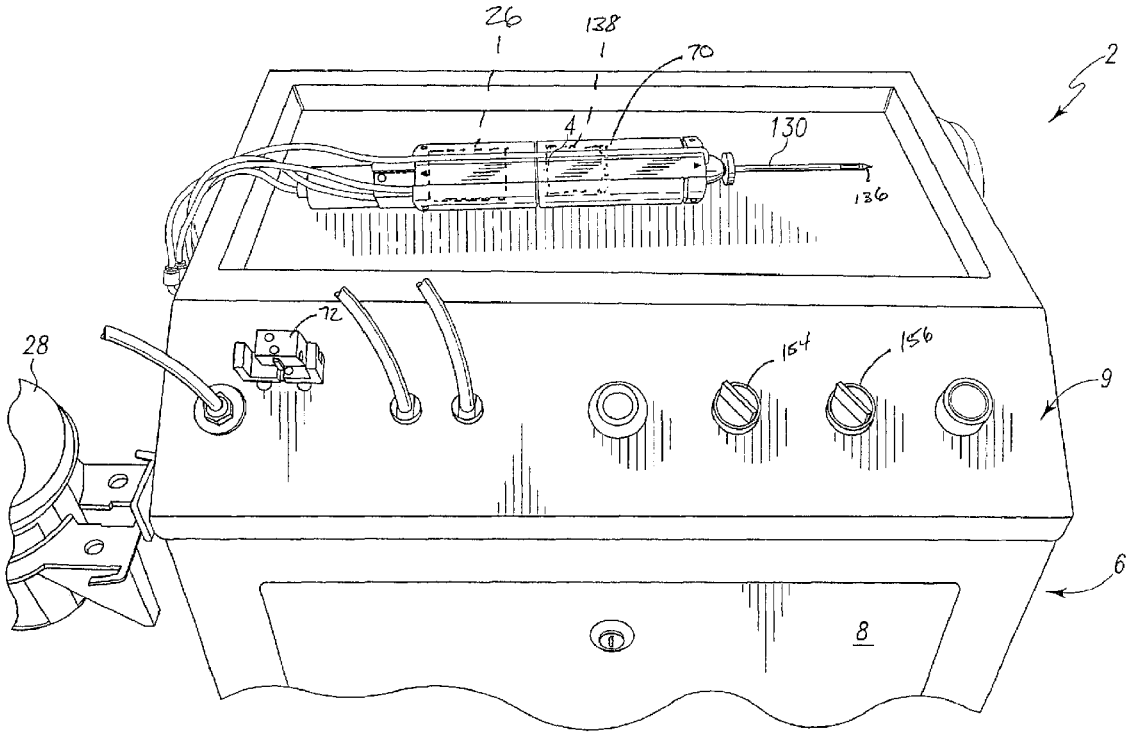

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-13 are cancelled.

\* \* \* \* \*